United States Patent
Adams et al.

(10) Patent No.: US 10,347,361 B2
(45) Date of Patent: Jul. 9, 2019

(54) GENOME EXPLORER SYSTEM TO PROCESS AND PRESENT NUCLEOTIDE VARIATIONS IN GENOME SEQUENCE DATA

(71) Applicant: NantOmics, LLC, Culver City, CA (US)

(72) Inventors: Julie Adams, Pleasanton, CA (US); Mirko Buholzer, Cupertino, CA (US)

(73) Assignee: NantOmics, LLC, Culver City, CA (US)

( * ) Notice: Subject to any disclaimer, the term of this patent is extended or adjusted under 35 U.S.C. 154(b) by 85 days.

(21) Appl. No.: 14/062,234

(22) Filed: Oct. 24, 2013

(65) Prior Publication Data

US 2014/0115515 A1    Apr. 24, 2014

Related U.S. Application Data

(60) Provisional application No. 61/717,773, filed on Oct. 24, 2012.

(51) Int. Cl.

| | | |
|---|---|---|
| *G16B 30/00* | (2019.01) | |
| *G16B 45/00* | (2019.01) | |
| *G16B 50/00* | (2019.01) | |
| G16B 20/00 | (2019.01) | |

(52) U.S. Cl.
CPC .............. *G16B 30/00* (2019.02); *G16B 45/00* (2019.02); *G16B 50/00* (2019.02); *G16B 20/00* (2019.02)

(58) Field of Classification Search
None
See application file for complete search history.

(56) References Cited

U.S. PATENT DOCUMENTS

| | | |
|---|---|---|
| 7,910,354 B2 | 3/2011 | Drmanac et al. |
| 8,053,191 B2 | 11/2011 | Blake |
| 8,278,039 B2 | 10/2012 | Drmanac |
| 2003/0204317 A1 | 10/2003 | Loraine et al. |
| 2008/0221832 A1 | 9/2008 | Drmanac |
| 2009/0105961 A1 | 4/2009 | Drmanac |
| 2009/0112871 A1 | 4/2009 | Hawthorne et al. |
| 2009/0318304 A1 | 12/2009 | Drmanac et al. |
| 2010/0161607 A1 | 6/2010 | Singh et al. |
| 2010/0227768 A1 | 9/2010 | Wigler et al. |
| 2010/0281401 A1 | 11/2010 | Tebbs et al. |
| 2011/0004413 A1 | 1/2011 | Carnevali et al. |
| 2011/0033854 A1 | 2/2011 | Drmanac et al. |
| 2011/0307553 A1 | 12/2011 | Ghang et al. |
| 2012/0030602 A1 | 2/2012 | Barrett et al. |
| 2012/0078901 A1 | 3/2012 | Conde |

FOREIGN PATENT DOCUMENTS

| | | |
|---|---|---|
| WO | 2014/090100 A2 | 10/2004 |
| WO | 2008/128111 A1 | 10/2008 |
| WO | 2011/090557 A1 | 7/2011 |
| WO | 2012/006291 A1 | 1/2012 |
| WO | 2012/051346 A1 | 4/2012 |
| WO | 2013/067001 A1 | 5/2013 |
| WO | 2013/086355 A1 | 6/2013 |

OTHER PUBLICATIONS

Dombrowski et al., "Chapter 20: Using the Map Viewer to Explore Genomces," The NCBI Handbook, pp. 1-24 (2002).
Fredman et al., "HGVbase: A Human Sequence Variation Database Emphasizing Data Quality and a Broad Spectrum of Data Sources," Nucleic Acids Research, 30(1): 387-391 (2002).
Krzywinski et al., "Circus: An Information Aesthetic for Comparative Genomics," Genome Research, 19(9): 1639-1645 (2009).
Rosenbloom et al., "Encode Data in the UCSC Genome Browser: Year 5 Update," Nucleic Acids Research, 41: D56-D63 (2013).
International Search Report and Written Opinion for PCT Application No. PCT/US2013/066612 dated Jan. 10, 2014.
Thorvaldsdottir et al., Integrative Genomics Viewer (IGV): high-performance genomics data visualization and exploration, Briefings in Bioinformatics, vol. 14. No. 2, Apr. 19, 2012, pp. 178-192.
Yang, et al., "An integrated database-pipeline system for studying single nucleotide polymorphisms and diseases," BMC Bioinformatics 2008, 9(Suppl 12):S19.
Dreszer, et al, "The UCSC Genome Browser database: extensions and updates 2011," *Nucleic Acids Res.* Jan. 2012;40(Database issue):D918-23.
Rosenbloom, et al, "Encode whole-genome data in the UCSC Genome Browser: update 2012," *Nucleic Acids Res.* Jan. 2012;40(Database issue):D912-7.
McEntyre et al., "The NCBI Handbook", pp. 341-363, Bethesda(MD): National Center for Biotechnology Information (US), Oct. 2002.
Chinese Patent Application No. 201380067867.2 filed Dec. 24, 2013, translation of First Office Action dated Dec. 26, 2016, all pages.
European Application No. 13849109.7, Partial supplementary European search report dated Jun. 13, 2016, 7 pages.

*Primary Examiner* — Joseph Woitach
(74) *Attorney, Agent, or Firm* — Kilpatrick Townsend & Stockton LLP

(57) ABSTRACT

This disclosure provides a technology for users to gain first-hand knowledge and experience with interpreting whole genomes. The technology graphically depicts variations in genome sequences in an expandable display, and provides a platform whereby the user may find and research the biological significance of such variants. The technology also provides a unique collaborative environment designed to capture and improve the collective knowledge of the participating community.

21 Claims, 16 Drawing Sheets

GENOME EXPLORER SYSTEM TO PROCESS AND PRESENT NUCLEOTIDE VARIATIONS IN GENOME SEQUENCE DATA

CROSS-REFERENCE TO RELATED APPLICATION

This application is a non-provisional of and claims the priority benefit of U.S. provisional application 61/717,773, filed Oct. 24, 2012. The priority application is hereby incorporated herein in its entirety for all purposes.

FIELD

This disclosure relates generally to the field of genome sequence analysis. More particularly, computer systems and methods are described that provide a graphical display of sequence variations and that can be integrated with a network to promote publication and community feedback.

BACKGROUND

Methods for whole genome sequencing have been described, for example in U.S. Pat. No. 7,910,354 (arrays of amplified polynucleotides), U.S. Pat. No. 8,278,039 (random array DNA analysis by hybridization); US 2009/0318304 A1 (efficient shotgun sequencing methods); and US 2011/0033854 A1 (long fragment read sequencing). Methodology for assembling DNA sequence fragments into extended genomic sequences includes but is not limited to the methodology described in U.S. Pat. No. 8,053,191 (iterative nucleic acid assembly using activation of vector-encoded traits); US 2011/0004413 A1 (calling variations in a sample polynucleotide sequence with respect to a reference polynucleotide sequence); US 2009/0105961 A1 (methods of nucleic acid identification in large-scale sequencing); and US 2008/0221832 A1 (methods for computing positional base probabilities).

Besides determining a genome, it is beneficial to be able to visualize the genome in an efficient and intuitive manner.

BRIEF SUMMARY

This disclosure provides a computer system and method for determining, displaying, and discussing variations that occur in genetic sequences between different individuals.

One aspect of the invention is a method for displaying variations between genomes between different individuals of the same species, and differences between other complex sequences. Sequence data is received for a test sample and a reference sample, the samples are aligned using a computer system, and variations in sequence are identified. The variations can then be displayed on a comparative gene sequence map showing where the variations are located. The user can be provided with an interface for controlling display of the comparative gene sequence map. The user can select from the interface a selection of a region within the genetic sequence map (sometimes less than half the entire comparative gene sequence map), whereupon the display is reconfigured such that the region is magnified, optionally in proportion to the size of the region: for example at least two times the original display, presented across at least about one half of the width of the display.

A display system according to the invention may be configured to display sequence and variant data in several formats. The formats may include a karyogram view, a cytogenomic view, a chromosome linkage view, a chromosome view, a linear map, or a sequence view, typically with any combination of several or all of these formats available and user selectable.

The gene map can provide resolution down to the level of single bases. Thus, the method comprises determining whether the region is smaller than a specified size, and if so, displaying a nucleotide sequence that spans the region, and (should at least one of the determined variations occur within the selected span at the specified size), displaying the locations of the variations with respect to the nucleotide sequence. Gene variations for display according to the method include but are not limited to copy number variations (CNVs), small nucleotide variations (SNVs), loss of heterozygosity (LOH), and other variation types listed elsewhere in this disclosure.

Richness of the display can be adapted to the liking of the provider and/or the user. For example, the display can present separate graphs across the region of interest for copy number, allele specific copy number, and protein encoding sequences. The user may be given the capacity to select a karyogram view, a circular view across one or more chromosomes, or a linear view of a region of interest, any of which indicate where variations in complex sequence occur.

To provide secure access to complex sequences of test samples, the method may comprise receiving a first identifier identifying a user and a second identifier identifying a test sample, determining whether the user has authority to access sequence data for the test sample, and if so, retrieving complex sequence for the test sample from a secure database, the secure database including genomes for a plurality of different samples. The method may also comprise doing the actual sequencing of DNA contained in the test sample, using any suitable method, such as those listed elsewhere in the disclosure. The reference sequence can optionally be selected from a database of such sequences, for example, by sourcing complex sequence for any one of a plurality of a reference samples in a reference database; comparing the complex sequence for the test sample with the reference sequence, and selecting a reference sequence if it matches the test sample according to preset criteria.

Filtering of the data can be done by receiving a selection of a filter that specifies characteristics of sequence variations to be displayed; and adapting the display to highlight variations having the characteristics and/or remove variations not having the characteristics specified by the filter. The method may comprise predicting one or more effects of sequence variations on protein expression, protein function, clinical presentation, or disease risk, and providing information about the effects with the gene sequence map. The method may also compare at least some of the variations with known variants, and providing information about the known variants with the gene sequence map, optionally from external databases. Certain variants can be highlighted or pinned by the user by receiving a selection of one or more of the variations in DNA sequence, and indicating the one or more variations on the comparative genetic map. The method may comprise receiving a selection of one or more of the variations in DNA sequence, determining the position of each of the selected variations in the human genome, obtaining information about DNA sequence variations observed for other samples at or around the position for at least some of the selected variations, and providing a display comprising the information.

Another aspect of the invention is a computer product comprising a non-transitory computer readable medium storing a plurality of instructions that when executed control a computer system to perform any aspect of the aforedescribed method.

Another aspect of the invention is a system configured to calculate and provide a display of variations in complex sequence data of a test sample relative to complex sequence data for a reference sample according to methods described herein. The system may comprise a computer processor, a database storing the reference DNA sequence data, and a DNA sequencer. The system may be configured so that the user may share information with others about one or more variations.

Another aspect of the invention is a server system for sharing variations in complex sequences between clients. The system comprises one or more processors configured to assemble a display such as a gene sequence map that shows a plurality of variations between a sample complex sequence for a test sample and a reference complex sequence for a reference sample. The processors provide the gene sequence map to a plurality of clients; provide a first user interface to a first client, wherein the user interface is configured to receive directions to make the gene sequence map available to other clients, and receive first information about one or more of the variations made available to the other client. The system is configured to provide a second user interface to one or more second clients; receive reply information from the one or more second clients about the one or more variations made available; and provide, to the first client, the reply information for the one or more variations.

The system may provide the gene sequence map to the plurality of clients with links from one or more of the variations to first information and reply information for the respective variation. The first information about the one or more variations provided by the first client user can be made available to other clients with hyperlinks that link to an indication of the one or more variations on the gene sequence map. The first information can be displayed in a feed as one or more entries, the feed being available to a plurality of users, wherein each entry corresponds to a respective variation. The first information about the one or more variations can be made available to the other users by way of an information website on the Internet. The server can be configured to compile reply information about one or more of the variations from other users into an assessment as to whether the variations are pathogenic or benign.

Other aspects of the invention will be evident from the description that follows.

Definitions

The terms "complex sequence", "sequence compilation" or "target sequence" as used in this disclosure refer to a set of nucleotide sequences for an individual or combination of individuals of any species. The sequence data may be obtained by sequencing a biological sample from a particular individual, or it may be constructed as artificial or consensus sequence data for a human individual or population. The complex sequence may be complete or partial genome sequence data, it may be cDNA sequence data from an expression library, it may be a sequence collection such as an exome or a biome, or it may be another DNA compilation of interest to the user. Unless explicitly stated otherwise, a suitable individual from which the complex sequence has been obtained may be selected from a human, other mammals, other vertebrates, other eukaryotes, prokaryotes, or combinations thereof, including but not limited to a pool of human or other biological samples from a particular source or from a particular human subclassification, single celled organisms from a particular environment, or a compilation of consensus or hypothetical sequences of an organism or component thereof.

A "reference sample" as used in this disclosure is any sample to which the user may compare a test sample, as explained below. The reference sample can have a reference complex sequence, e.g., a reference genome. A sequence of a nucleic acid molecule from the test sample (thus corresponding to the genome of the test sample) can be aligned to the reference sequence.

A "comparative gene sequence map" is a graphical depiction in which variations between two or more complex sequences are mapped between genetic position indicators (such as base count or known markers) along a DNA structure such as a chromosome. Unless otherwise specified, gene sequence maps provided for display are "expandable", in the sense that the user may request depiction of an overview (such as an entire chromosome), or a segment thereof in increasing detail, ultimately resolving into the actual nucleotides in the sequence in the selected segment.

Nucleotide sequence "variations" include any difference between a complex sequence (e.g., a genome) of one sample and the complex sequence of another sample, as determined from sequence reads of the respective samples, which is explained and exemplified below.

A "display" is a visual depiction shown on an I/O device such as a monitor or touchpad, or within a frame or window depicted by the device. A computer system may "provide a display" of an item, for example, by causing the item to present on a suitable output device operatively connected to the system, or by sending to an external device (such as a client) a set of data that will enable the device to present the item locally.

DETAILED DESCRIPTION

Figure 1A:
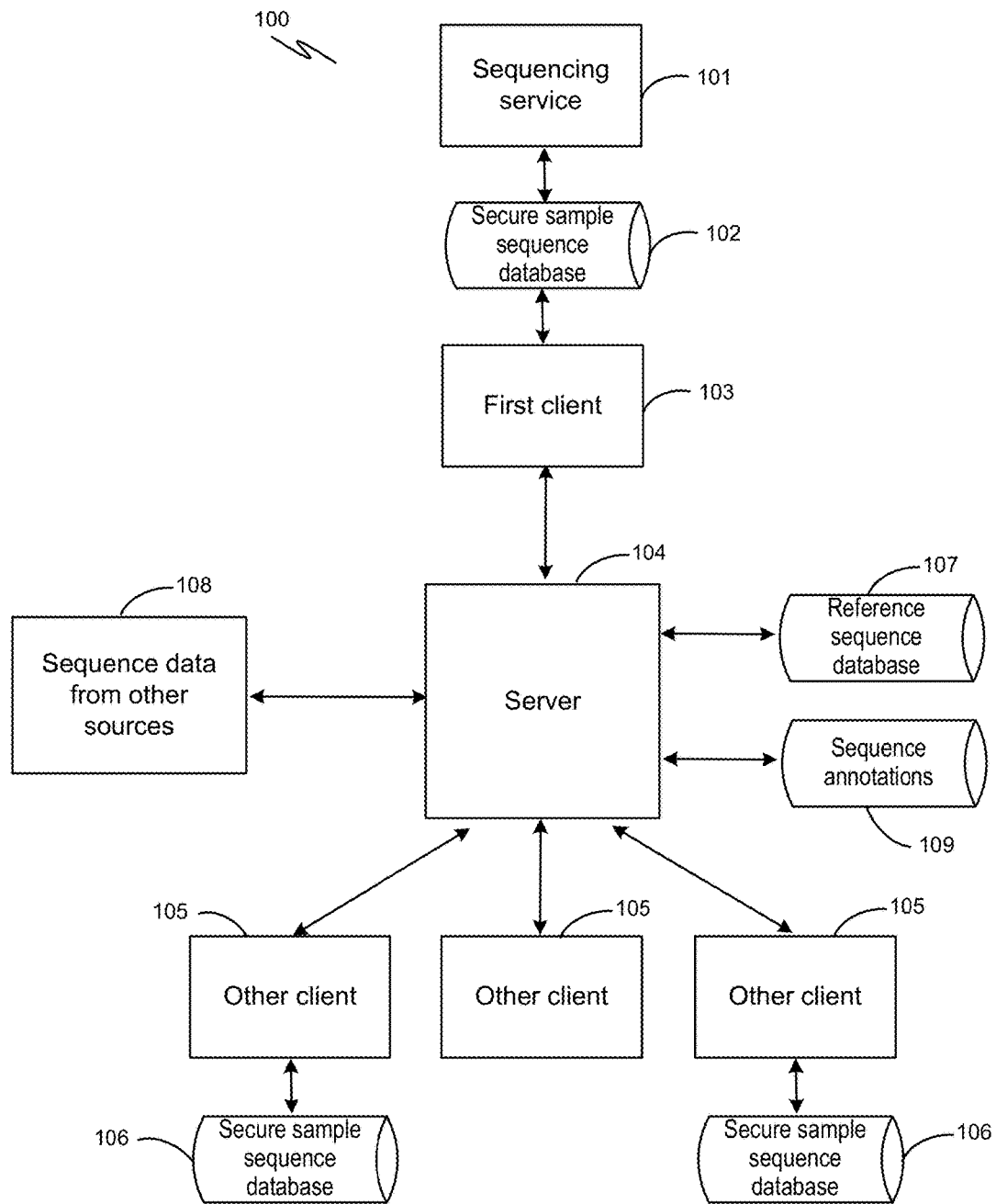
FIG. 1A is a block diagram with an exemplary configuration for a gene explorer system according to this invention.

This disclosure provides a technology for users to gain first-hand knowledge and experience with interpreting whole genomes. The technology graphically depicts variations in genome sequences in an expandable display, and provides a platform whereby the user may find and research the biological significance of such variants. The technology also provides a unique collaborative environment designed to capture and improve the collective knowledge of the participating community.

By way of illustration, each user may analyze one or more complex sequences in the following fashion. After presenting their credentials, the user calls from a client for a complex sequence obtained for a test sample and stored on a secure database accessible by the sever. The system matches the test sequence to a selected reference sequence. The test and reference sequences are aligned, and sequence variations are determined. The variations are mapped on the sequence in a graphical display which is provided to the user by way of the client. The user may explore regions of interest on the map by directing the system to move about and expand the display. The user can drill down to review gene variations at the nucleotide level. The user can also request that the data be filtered for particular genes or particular types of variations.

The computer system also provides a platform by which the user may authorize other users to have access to the test sample sequence, and the genetic variations determined therefrom. Both the primary user and other users may annotate the variations and exchange comments over a social network that is integrated into the system.

I. Overview

Whole human genome sequencing holds great promise as a diagnostic and predictive aid in the management of human health. However, interpreting whole genome data to obtain clinically instructive information poses substantial challenges. Before development of the technology described here, expertise in analyzing and interpreting genome sequence data has been distributed across a variety of genomic databases, making it difficult to assemble different sorts of information and resolve open questions by consensus. The technology described here addresses these challenges by consolidating information from multiple sources, and providing a platform for more users to learn and share knowledge about interpreting genomic variants.

The technology described here provides a number of important advantages over what was previously available. First, the sequence analysis system described here can be integrated with a service for determining genomic sequence of a biological sample. The new sequence data can be consolidated with information from multiple sources, including prediction algorithms and cross-reference annotations from external genomic databases. Second, the technology helps users interpret genomes by providing users with important and instructive information through an easy-to-use interface.

Third, the technology allows experts to collaborate across the platform. In the tradition of modern electronic networks where people connect and share ideas in business and their personal lives, the technology described here has a collaborative function specifically focused on the interpretation of genome sequence variants This creates a vibrant knowledge base in genomics, to the benefit of clinician researchers everywhere and the patients under their care.

FIG. 1A is a block diagram showing an illustrative configuration for a gene explorer system 100 according to this invention A first user accesses the system through a first client computer or terminal 103 operatively connected to a local or network accessible server 104. The client 103 has access to and provides sequence data from a database 102. Typically, the database 102 is secured to protect confidentiality or control access of sequence data obtained from a sequencing service 101, obtained for example by sequencing one or more biological test samples. The secure sample sequence database 102 may be connected independently to the client computer 103, or it may be a partition of a shared database connected with the server 104 to which the user controls access. The server processes data from the database 102 so as to create a display for presentation on the client computer 103. The processing typically includes comparing the test sequence with one or more reference sequences, such as a consensus sequence in a region of interest with respect to a particular disease or condition. The reference sequences used in the analysis may be stored on a reference sequence database 107 compiled by the server, and/or obtained from an external source 108.

Each variation identified between a test sample and a reference sample may be analyzed by the server 104 with a plurality of filters or algorithms (for example, to determine if it causes a change in the encoded protein), and annotated accordingly. Each variation may be compared with previously known variations, and annotated according to the clinical or academic significance of the previously known variant. The annotations (or a selection thereof) are each provided at or near the respective sequence variation displayed on the client computer 103. In some configurations of the invention, the user has the option of making the test sequence available to one or more other users having their own client 105 connected to the server 104. Each of the other users may or may not bring their own sequence of interest from a client-specific database 106 for purpose of comparison or analysis. Information from the other clients 105 may be used by the server 104 to annotate the display presented on the first client 103. The server 104 may also provide a forum whereby the first user and the other users may exchange written commentary with regards to variations observed in the test sample.

Figure 1B:
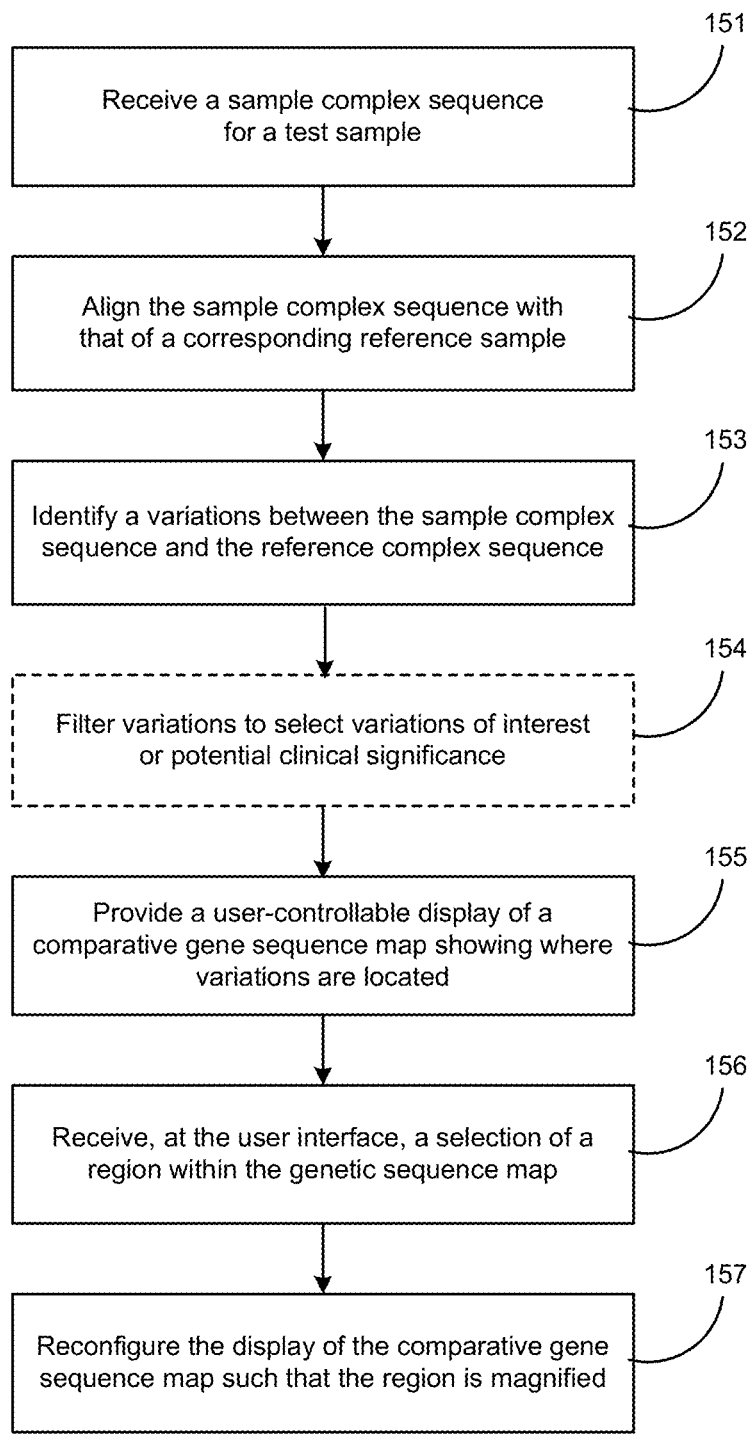
FIG. 1B is a flow chart showing a process by which a user may have the system analyze and display sequence data.

FIG. 1B is a flow chart showing a process by which a user may submit a sequence for processing and obtain a display according to this invention. Features of this process are described below in Section III.

The methods and systems described here can be used for a variety of research purposes and techniques. One such application is to assist a user in evaluating genetic variations that may be present in the genome, diseased tissue, or expression library of a particular individual. Such information may be instructive in the clinical management of the individual's underlying condition.

Thus, the user may obtain and upload a complex sequence from test sample into the system before analysis. Another application of the technology is to integrate the analytical tools with a DNA sequencing service, whereupon sequence information obtained from a particular individual becomes the subject of the analysis.

Sequencing methodology suitable for use with this invention includes but is not limited to the methodology described in U.S. Pat. Nos. 7,910,354; 8,278,039; US 2009/0318304 A1; and US 2011/0033854 A1. Generally, complex sequence is fully assembled before being used to identify sequence variations as described here. Methodology suitable for assembling DNA sequence fragments into extended genomic sequences includes but is not limited to what is described in U.S. Pat. No. 8,053,191; US 2011/0004413 A1; US 2009/0105961 A1; and US 2008/0221832 A1, which are here incorporated herein by reference in their entirety for all purposes.

Complex sequence from a test sample can be loaded from the sequencing apparatus into the analytic system of this technology automatically, by the system operator, or by the end user. The system can be configured with a security system so that each user may control access to complex sequences from each sample. The user may be provided with the sequence data in electronic form, and then the source data is expunged from the server. More conveniently, the server may provide a repository of data, so the user may access the data on the server by cloud computing, and thereafter apply the analytic tools of this invention to the data from each test sample at the user's convenience.

To maintain access control, for example, the server can be programmed to receive a first identifier identifying a user and a second identifier identifying a test sample. It then compares the identifiers with stored information to determine whether the user has authority to access sequence data for the test sample. If the requesting user has such authority, the server then retrieves complex sequence for the test sample from a secure database, and permits the user to view, analyze, and optionally download the data. The user may also have authority to change permissions, such that access to the complex sequence data and/or the subsequent analysis is opened up to other specified users or class of users, other members of having access to data on the server, or the public at large.

II. Identification and Display of Sequence Variations

In order to determine variations in the sequence, the system can compare the complex sequence from the test sample with complex sequence from a reference standard. After receiving complex sequence for a test sample, the system aligns the complex sequence for the test sample with complex sequence for one or more reference samples, so that substantially identical portions of sequence are compared. Differences between the test sequence and the reference standard are identified by the system as variations, which may then be filtered as described below as an aid to evaluating their biological and clinical significance.

The reference standard used for this analysis may be consistent for all test samples during a period of operation. Alternatively the reference standard may be provided or identified by the user for the analysis of a particular test sample. This may be useful, for example, in the analysis of tissue from a tumor, where normal or unaffected tissue from the same person may serve as the closest reference.

In some implementations, the server will have access to a plurality of potential reference standards, and the server will identify one or more references to be used for each test sample analyzed by the system. In this implementation, the system will source complex sequence for any one of a plurality of standard samples in a reference database. It will compare the complex sequence for the test sample with the complex sequence called from the reference base. It can then select a standard from the database if the standard sample matches the test sample according to preset criteria.

A. Identification of Sequence Variations

Methods and systems of this invention can be used to identify variations in complex sequence. These are differences between the complex sequence of one or more test samples and one or more reference samples.

Nucleotide sequence variations include any difference between a sequence determined for one sample and the genome of another sample, as determined from sequence reads of the respective samples. Apparent variations may arise from errors in sequencing and/or sequence assembly. Where a variant is known or suspected of being a sequencing error, it may be suppressed or de-emphasized in the map displayed to the user. True sequence variations between a test sample and a (those reproducible upon resequencing or otherwise suspected or confirmed) include but are not limited to the following:

Small nucleotide variations (SNVs) and single nucleotide polymorphisms (SNPs). SNVs include the change, addition or deletion of one or more nucleotides in or around the region of variation. SNPs are a subset of SNVs wherein the variation of a single nucleotide occurs with known regularity between different individuals or different types of samples of the same species. SNPs include inheritable alleles and mutations in diseased tissue that occur with known regularity.

Copy number variations (CNVs), where a particular gene or other functional element of a complex sequence is replicated or reduced in replicates compared with a reference sample, such as may occur through gene duplication and/or translocation.

Loss of heterozygosity (LOH), chromosome trisomy and gene rearrangement (transposition). Embodiments of the invention can cause any one, some or all of such types of variations to be displayed in any combination.

The reference sample may be any sample to which the user may compare a test sample. It may be a sample of another individual, but is more typically a consensus or hypothetical sequence, such as may be created by amalgamating the corresponding sequences of a plurality of individuals, and/or editing to exclude or include one or more nucleotide variations for the purpose of the comparison. The comparison can be done by aligning the test sequence with the reference sequence so as to minimize the number of variations. For example, the test sequence can be aligned to a location that results in the fewest mismatches or variations from the reference sequence.

The reference sample may be selected from a database of reference samples to match the sample being analyzed. A reference sample is chosen to match a test sample if it is sufficiently similar to the test sample in terms of one or more preset criteria. By way of illustration, determining a match may include any one or more of the following criteria in any combination: degree of identity, present or absence of particular sequence variations of interest, and source information such as racial background, family relatedness, and clinical condition.

B. Display of Sequence Variations

The technology described here provides a platform by which users may visualize, filter and analyze variations in genomic sequence data in one consolidated tool. For example, small nucleotide variations (SNVs), copy number variations (CNVs) and loss of heterozygosity (LOH) events can all be viewed on the same display. A built in genome browser is provided to visualize and surf genomes with genome wide views down to base pair level views, so that the user may explore sequence variations that are relevant to their particular clinical situation.

As an introduction to results of the analysis and to orient the user, the system can provide the user with the choice of various views of the genome or expression library as a whole.

Figure 2A:
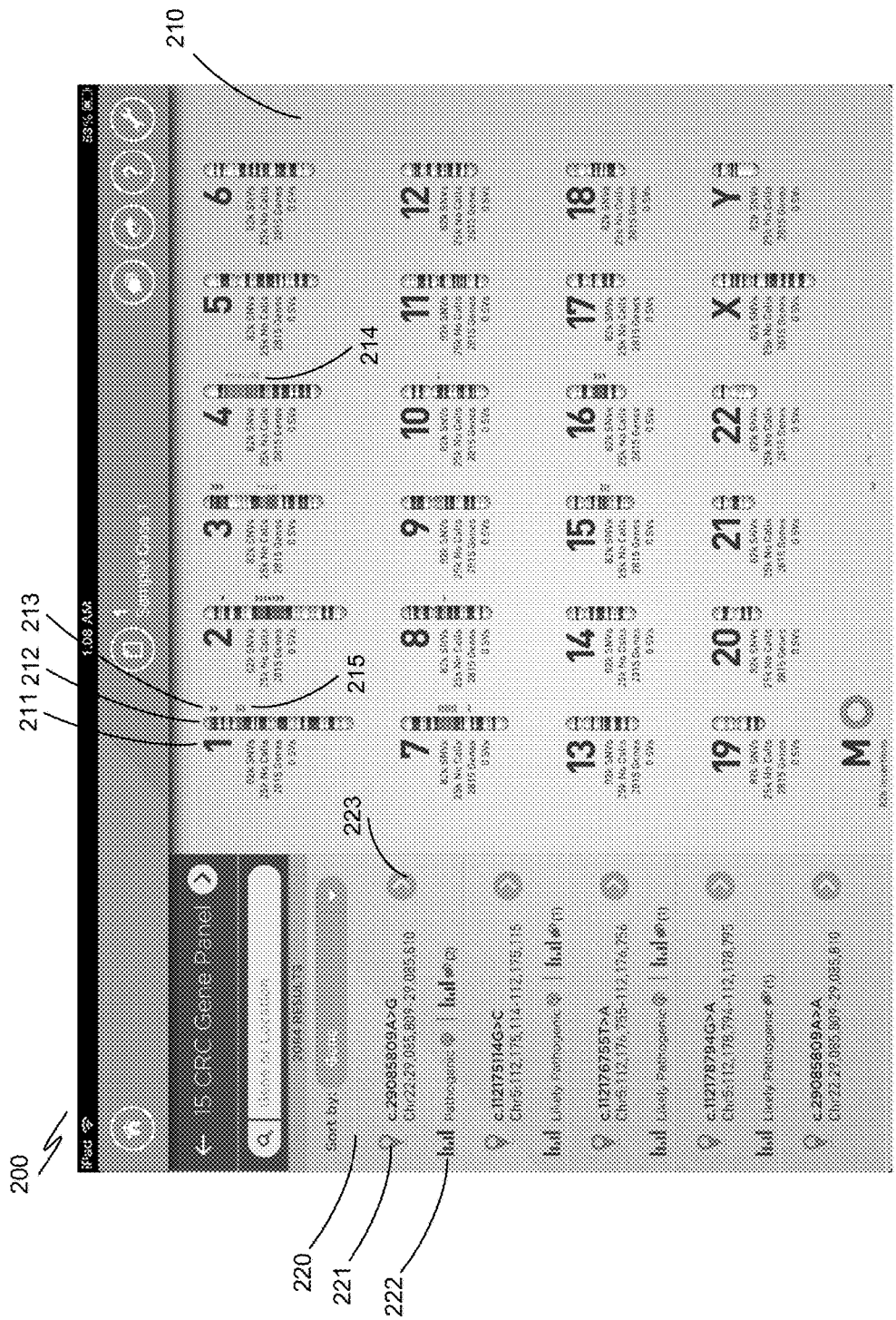
FIG. 2A is a screenshot showing a display of genome sequence data from a particular patient in a karyogram view.

By way of illustration, FIG. 2A is a screenshot 200 showing a display of genome sequence data from a particular patient. On the right side is a karyogram view 210, with copy number variations shown to the right of each chromosome 211, depicted according to its banding pattern 212. Copy number variations are shown to the right of each chromosome: Copy number gain, shown as downward pointing chevrons 213, copy number loss, shown as upwards pointing chevrons 214, and loss of heterogeneity, shown as horizontal hash marks 215.

The display on the left side 220 provides a list of particular variations in a panel of genes of interest 221 which a user has selected for analysis, with a summary assessment underneath 222 as to whether it is pathogenic or benign. The gene panel is selected as described below, in reference to FIGS. 5A and 5B. Each variation is named 221 according to its mapped position in the reference sequence, and the change made. Thus, c.29085809A>G is a variant detected on Chromosome 22 of the reference sequence mapping to position 29,085,809, where the nucleotide A (alanine) in the reference sequence is changed to G (glutamine) in the test sequence. Prediction of whether a particular variation is likely to be pathogenic 222 is made on the basis of the expected change to an encoded protein sequence, experience of such a change in other instances, or other types of predictive analysis in any combination. The display also comprises an icon 223 by which the user may call up further details, such as the test sequence accession number, the reference sequence accession number or designation, the position, the gene or sequence common name or designation, its symbol, further information on the type of sequence variation or SNV, and the zygosity (homozygous or half).

Figure 2B:
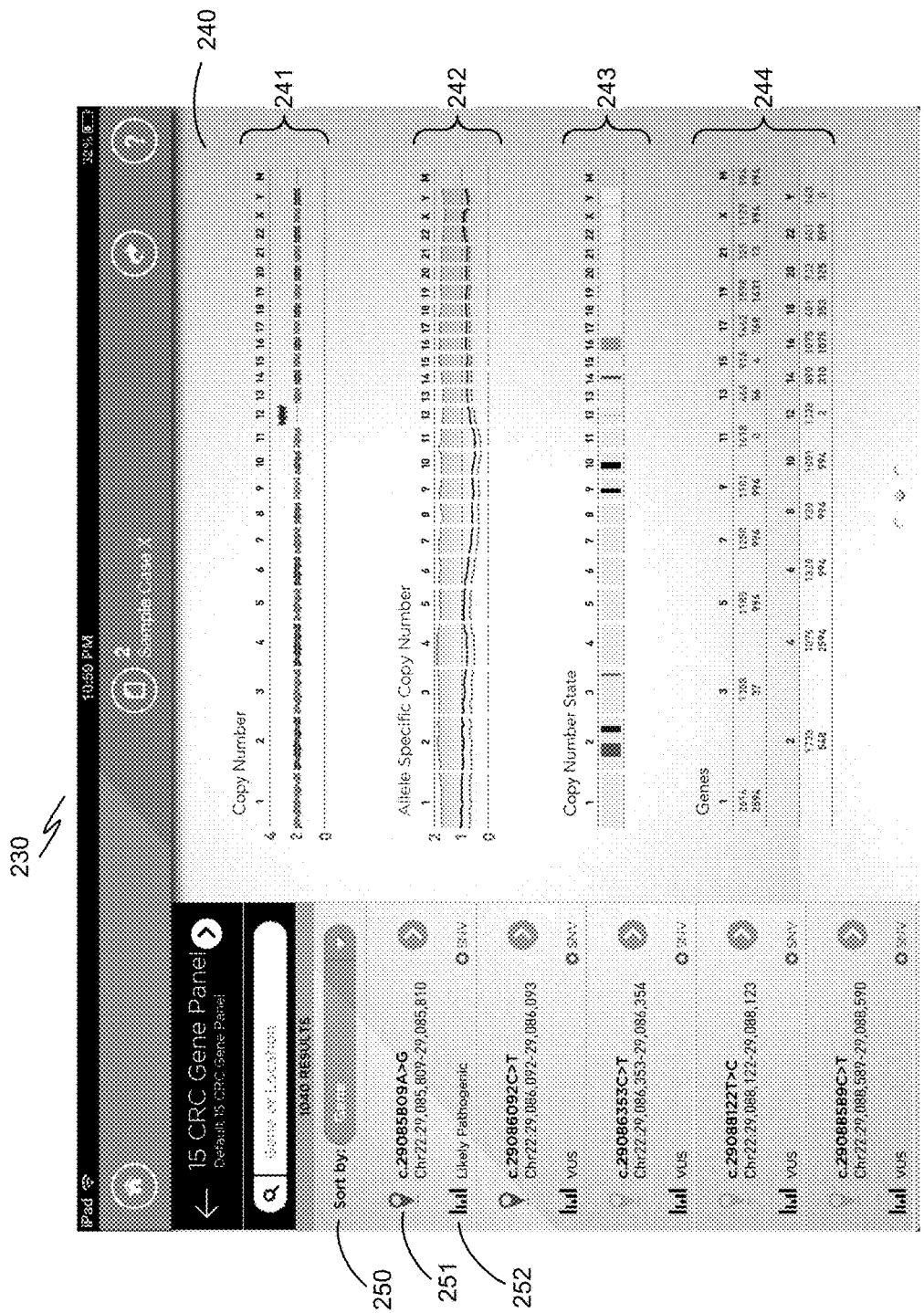
FIG. 2B shows a cytogenomic view of the entire genome, compared with a reference sequence.

FIG. 2B is another non-limiting illustration showing a screenshot 230 comprising a cytogenomic view. On the right side is a cytogenomic view 240 of the entire genome. Here, the data for each patient is compared with a sequence standard drawn from CGI's database. The top track 241 is copy number relative coverage data, which is the number of sequence reads of each region as a ratio of the coverage of the sample. The next track 242 is allele specific copy number which may show loss of heterozygosity (LOH) in a particular region due to a gene deletion or rearrangement event (for example, in cancer cells). The third track 243 shows a count of small nucleotide variations (which includes SNPs, inserts, deletions, and small substitutions) that occur in the gene panel selected by the user. The gene track 244 shows the concentration of genes across the genome. As the user zooms in to a particular region of interest, they will see the actual gene names as well as the exons and introns. On the left (as in FIG. 2A), there is a display 250 of known variations in certain genes of interest 251 that have been selected as a gene panel for assessing a particular condition, and a graphical assessment 252 as to whether the variations are predicted to be pathogenic or benign.

Figure 3B:
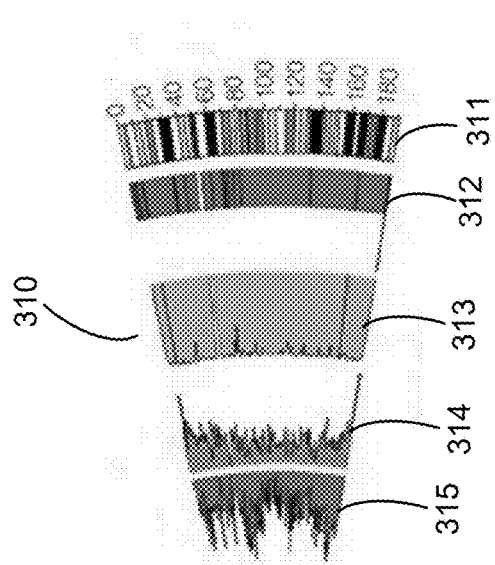
FIG. 3B is a more detailed view mapping nucleotide variations determined by comparing a test sequence with a reference sequence.
Figure 3A:
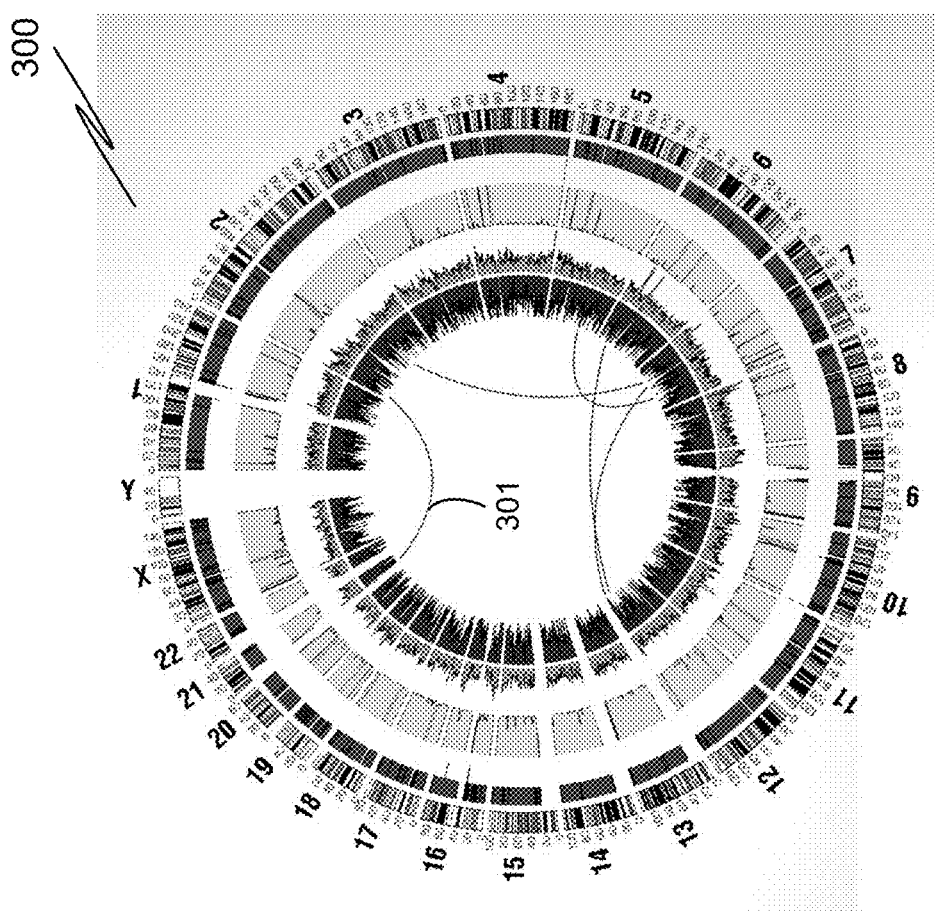
FIG. 3A is a display showing an overview of the entire genome sequence of the patient sample in the form of a Circos®-style plot, showing analysis of sequence variations and apparent interchromosomal junctions.

FIG. 3A is an overview display 300 of the entire genome sequence of the patient sample in the form of a circular or Circos®-style plot (M. Krzywinski et al., Genome Res. 19:1639-1645, 2009). This display shows the frequency of structural variations at locations across the chromosome map. Curved lines in the middle 301 show apparent inter-chromosomal junctions. FIG. 3B provides a detail 310 for Chromosome 4. From the outside in, the layers show a chromosome map 311, the called ploidy 312, the lesser allele fraction 313 (the fraction of the sample containing the allele that is present in ≤50% of the sample), heterozygous SNP density 314 (density of occurrence of SNPs as a single haplotype), and homozygous SNP density 315 (density of occurrence of homozygous SNPs).

III. Expandable Display

One aspect of the invention is a display system for surveying and analyzing complex sequence data. Referring back to FIG. 1B, the display system can receive sequence data 151, for example, new data inputted or transmitted to the system from a sequencing service that has determined the sequence of one or more biological samples of interest. One or more than two test sequences are aligned with one or more reference sequences 152 that are either standard to the analysis, or selected by the system or by the user as an appropriate match for the test sample. Such references may be stored within a database of reference sequences that have been stored or compiled by the system and/or retrieved from one or more external sources. The system may optionally update one or more reference sequences in the database on an ongoing basis as a learning function in relation to test sequences that are processed by the system Once the samples are aligned, the system then processes the data to determine where there are variations 153 between the test sequence(s) and the reference sequence(s). Variations include but are not limited to small nucleotide variations (SNVs), copy number variations (CNVs), loss of heterozygosity (LOH), and translocations. The variations that are identified by the system can optionally be filtered 154 to facilitate interpretation of the analysis. For example, one or more filters cam be implemented to exclude variations identified or suspected to be sequence read errors or assembly errors. As described elsewhere in this disclosure, other filters that can be implemented by choice of the use include but are not limited to filters that focus the display on particular genes or gene regions, filters that select variations depending on their effect on the function of the sequence (for example, the effect on an encoded amino acid sequence), and filters that select variations depending on previously known variants of particular interest or clinical significance. Such filters can be used singly or in any effective combination, and can be switched on and off by choice of the user during her review of the displayed data.

A display is then provided by the system 155 to a user client that show the filtered variations at their location on a map of the complex sequence: all the way from an overview map of the entire sequence (such as a karyogram view for a genomic sequence), in various degrees of detail down to the actual nucleotide sequence. The display is user controllable in the sense that (depending on how the system is configured), the user may request one or more of the following in any combination: a change in expansion or detail, the imposition or removal of filters, highlighting or annotating a particular variant identified by the system or a gene region comprising one or more variations of interest, and permitting other system users to provide their own annotations directly on the display or in a linked forum. In the configuration shown here, the user interface receives a selection of a region within a larger sequence map 156, whereupon the system reconfigures the display to magnify or focus on the region selected by the user. The user interface can also receive a request to decrease magnification or expand the scope of the region being analyzed, whereupon the system reconfigures the display to compress or scale down the previously viewed region into a smaller space so as to provide space for neighboring regions of the complex sequence to appear in the display.

Figure 4A:
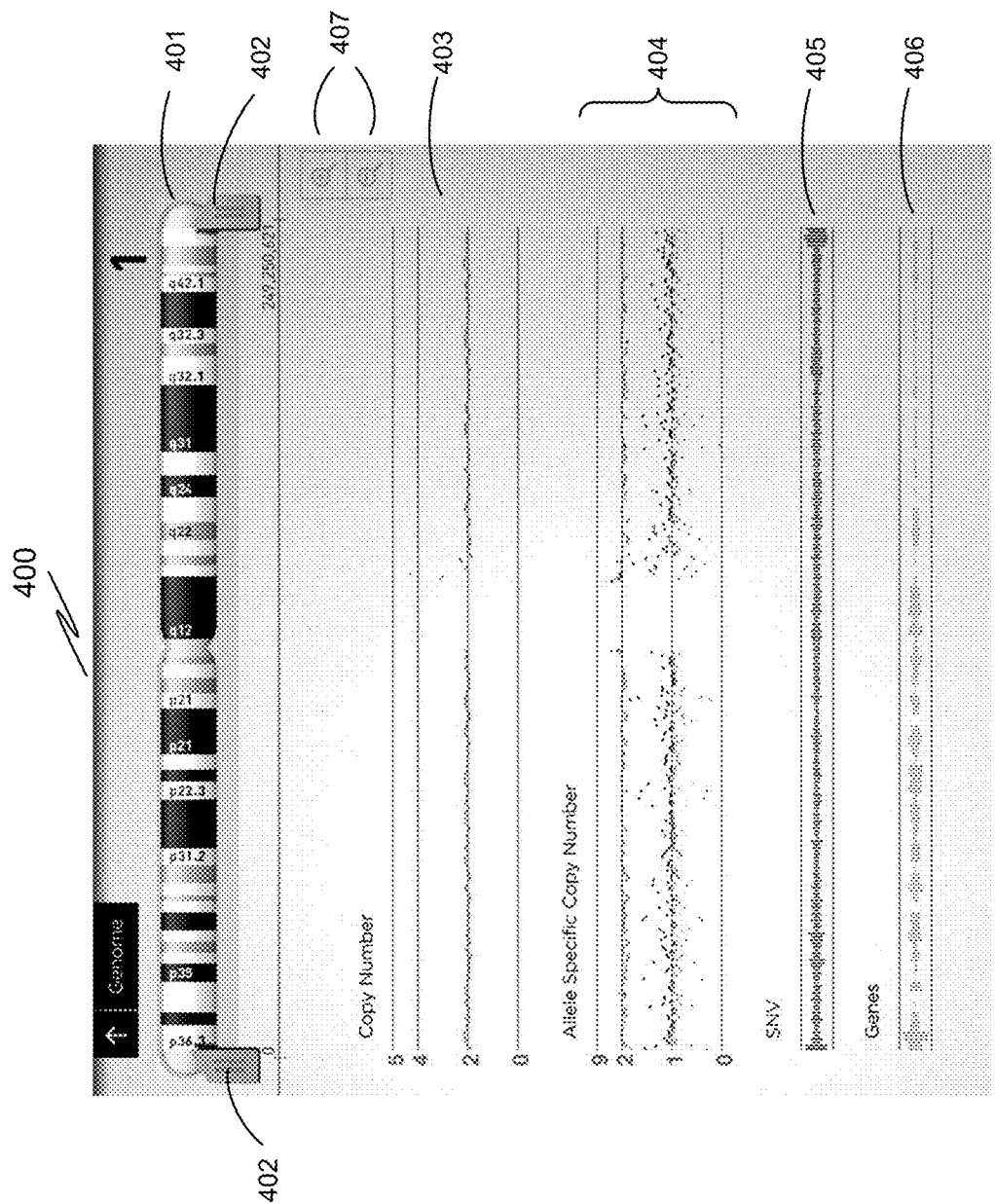
FIG. 4A is a display of Chromosome 1 in linear view, which can be expanded by moving the markers 402 to a narrower region for more detailed viewing.
Figure 4B:
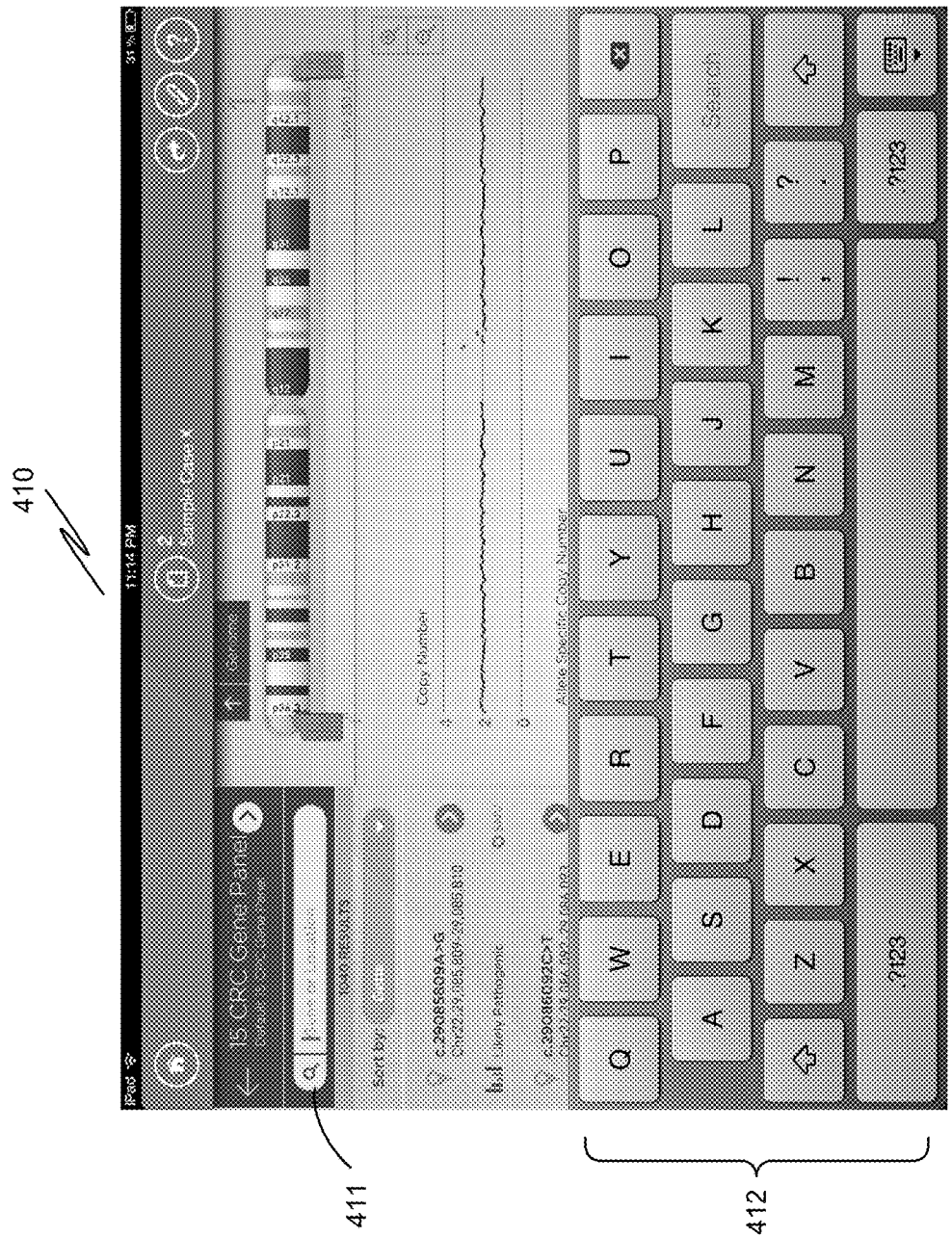
FIG. 4B shows a screenshot in which the user calls up a keyboard to input the name of a particular gene of interest for an exploded view.
Figure 4C:
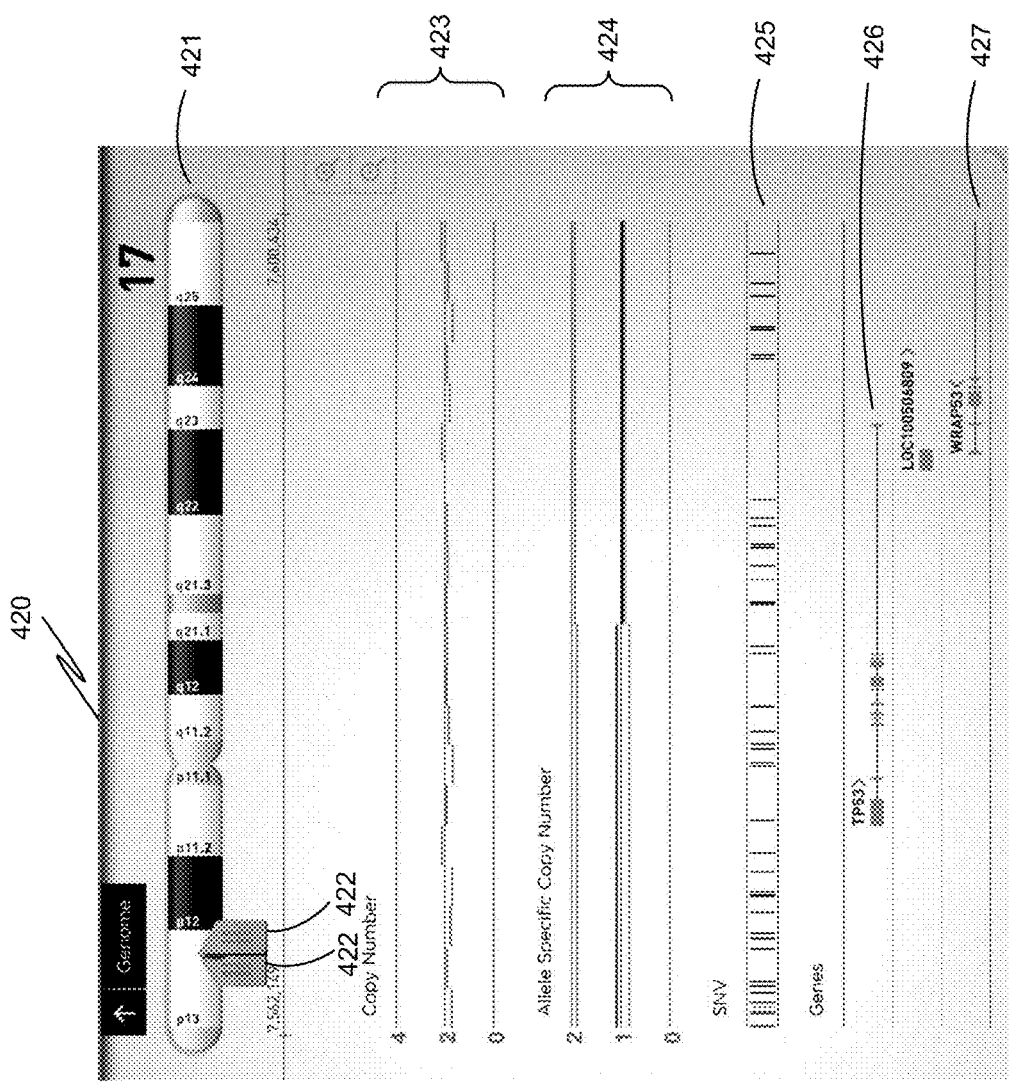
FIG. 4C shows a subregion of Chromosome 17, indicating the positions of genes TP53 and WRAP53, and single nucleotide variations (SNV).
Figure 4D:
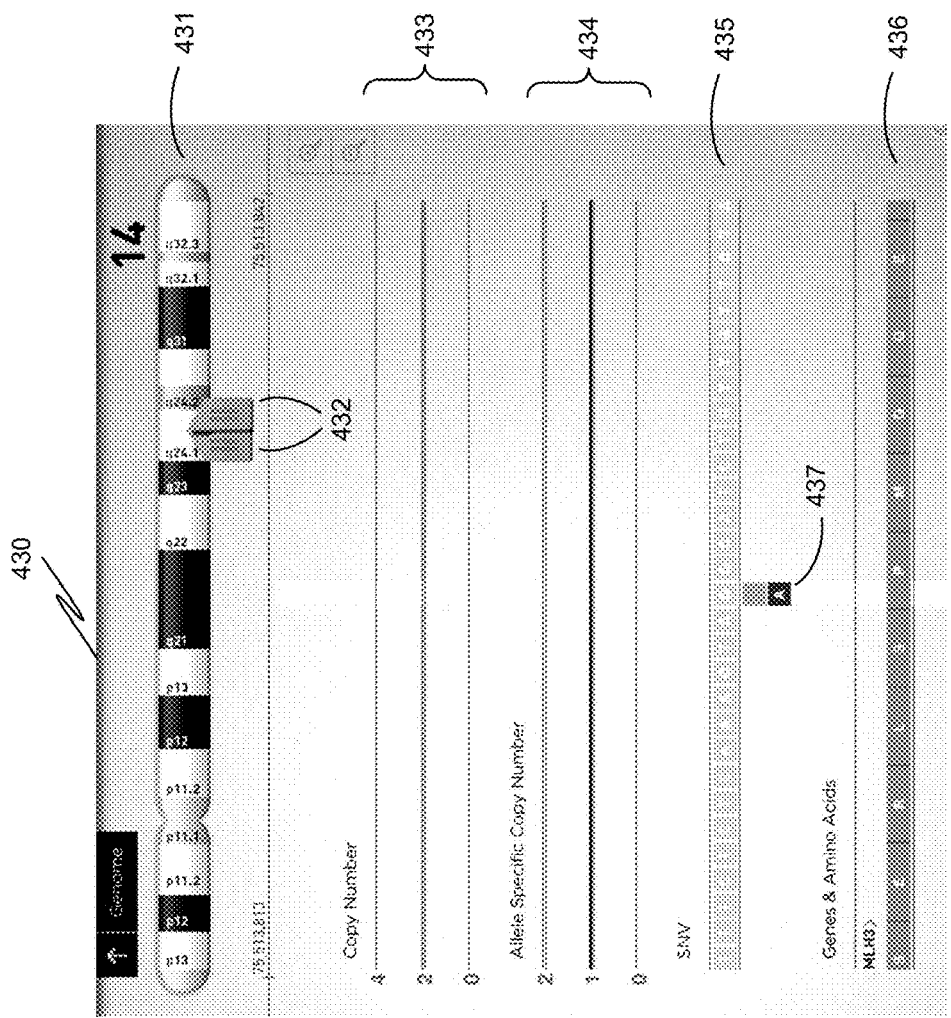
FIG. 4D shows a further expanded view of a particular gene on Chromosome 14. At this level of expansion, individual nucleotides of the genomic sequence are shown. The test sequence and reference sequence are the same, except where there is a variation: in this case, an SNV 437.

FIGS. 4A, 4B, and 4C illustrate the capacity of the display to drill down to subregions of interest to the user to inspect details of each sequence variation. The benefit of the expandable display is that it reconfigures in real time in response to user input so as to provide an expanded view of a particular region of interest. Thus, a genomic overview (such as FIG. 2A, FIG. 2B or FIG. 3A) can be expanded to detail a particular chromosome (FIG. 4A), shown here in a horizontally linear depiction. This in turn can be expanded to a particular subregion or gene cluster (FIG. 4C), and then to the area around and about one or more sequence variations of interest (FIG. 4D). The system maintains sequence data as the basis of the graphical display. Thus, if a sufficiently narrow region of interest is selected, the display will present nucleotide sequence on a nucleotide-by-nucleotide basis spanning the narrow region of interest. In this display, a small nucleotide variation (SNV) 437 can be identified as a particular nucleotide deletion, addition, or substitution in relation to the reference sequence.

Navigation between the views may be implemented in any way that is compatible with the underlying code and hardware. For example, the user may be provided with a numerical input or sliding scale to specify the degree of zoom from the original depiction. If the I/O device has a touch screen, then the view can be expanded, contracted, or moved up or downstream by touch, pinch, zoom, or tap at appropriate locations in the previous view. The interface may also be provided with links or menu choice whereby the user may specify a particular region, gene, variation, or other chromosomal feature, and be taken to a view whereby the selected feature occupies at least 10%, 20%, 40%, a majority, or substantially all of the width of the display. The system can also be configured so that the user has the option of pulling up a keyboard (FIG. 4B) through which to input the name of a particular gene or region upon which the display should be focused.

IV. Filtering and Data Interpretation

Genomes from different individuals who are not related inevitably comprise a range of sequence variations that provide a genetic basis for their individuality, but which do not necessarily portend a particular phenotype or disease susceptibility. Depending on the quality of the sequencing, there may also be sequencing errors that create noise potentially obscuring important data. To aid the clinician researcher in focusing on the variations more likely to be clinically significant, the system can provide a filtering capability to narrow the range of exploration.

Figure 5A:
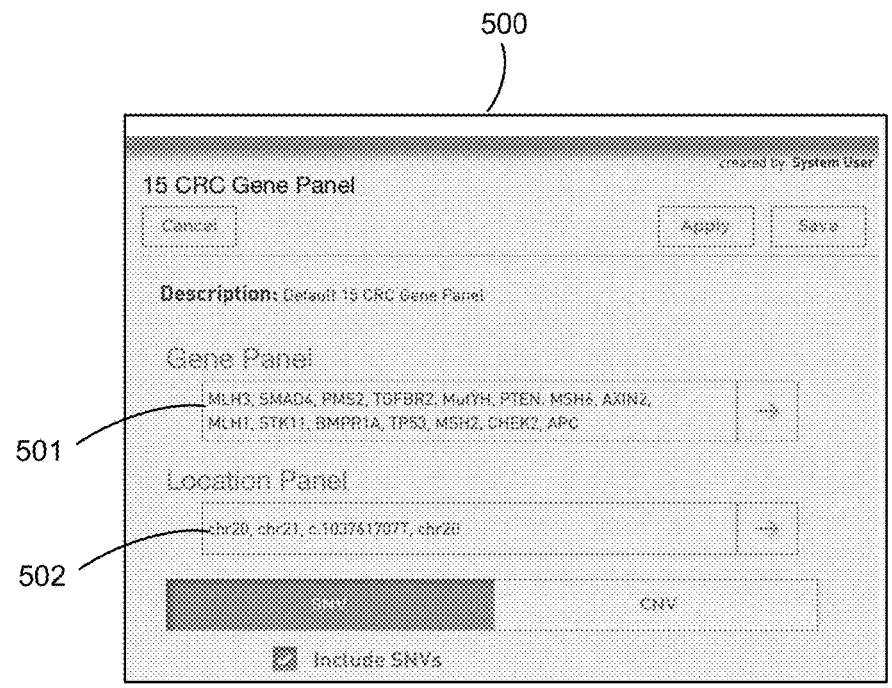
FIG. 5A shows a menu to filter the analysis towards specific genes or specific chromosomal locations of interest or potential importance.

FIGS. 5A, 5B, 5C, and 5D provide some non-limiting examples of the types of filters that can be implemented. In FIG. 5A, the user may focus the analysis towards certain genes 501 or specific chromosomal locations 502.

Figure 5B:
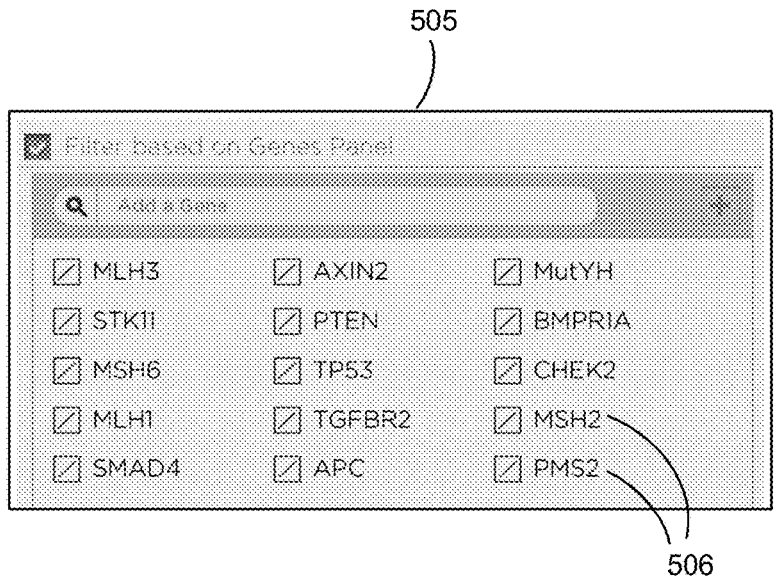
FIG. 5B shows a menu for assembling a gene panel.

In FIG. 5B, the user positively selects particular genes or gene categories of particular interest, from amongst a broad or comprehensive list of encoding regions, thereby forming a "gene panel". In this illustration, a panel of 15 genes known to be relevant for certain diseases or clinical conditions has been selected. The user has the option of selecting lists of between 1 and 10,000 genes, between 3 to 10,000 genes, between 5 to 1,000 genes, or between 10 and 100 genes. Instead of or in addition to selecting genes associated with a particular disease or condition, genes may be selected for the panel according to a selected functionality: for example, genes that encode cell surface receptors, or cell surface receptors specific for a certain ligand. The system can be configured to assist the user in selecting particular genes, or allow the user to select the entire category. In a similar fashion, the filter may permit the user to focus on non-encoding regions thought to be involved in another aspect of gene regulation, DNA processing, or biological phenotype. As another option, rather than selecting the genes one by one, the user or the system may utilize a predefined gene panel associated with a particular disease or condition of interest.

Figure 5C:
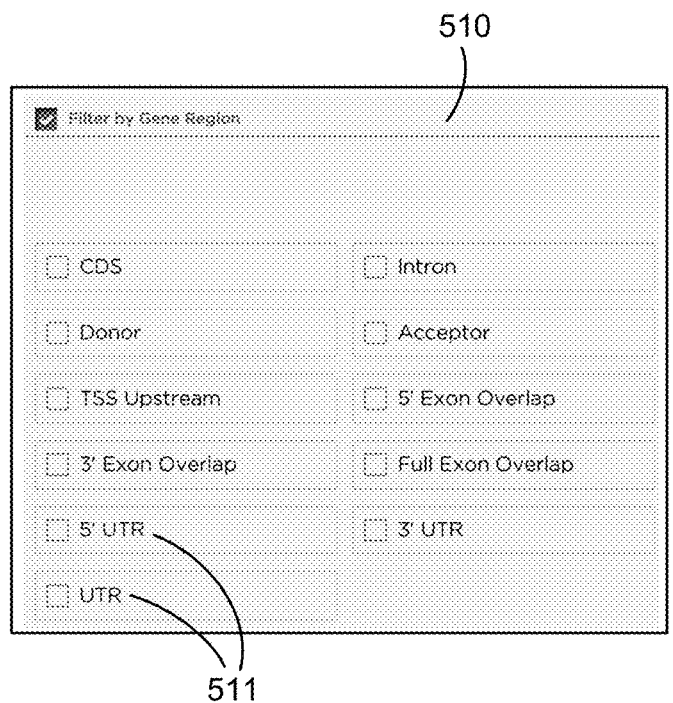
FIG. 5C shows a menu where the user selects chromosomal regions by function of the nucleotide sequence (for example, encoding regions, non-encoding regions within genes, and sequence between genes).
Figure 5D:
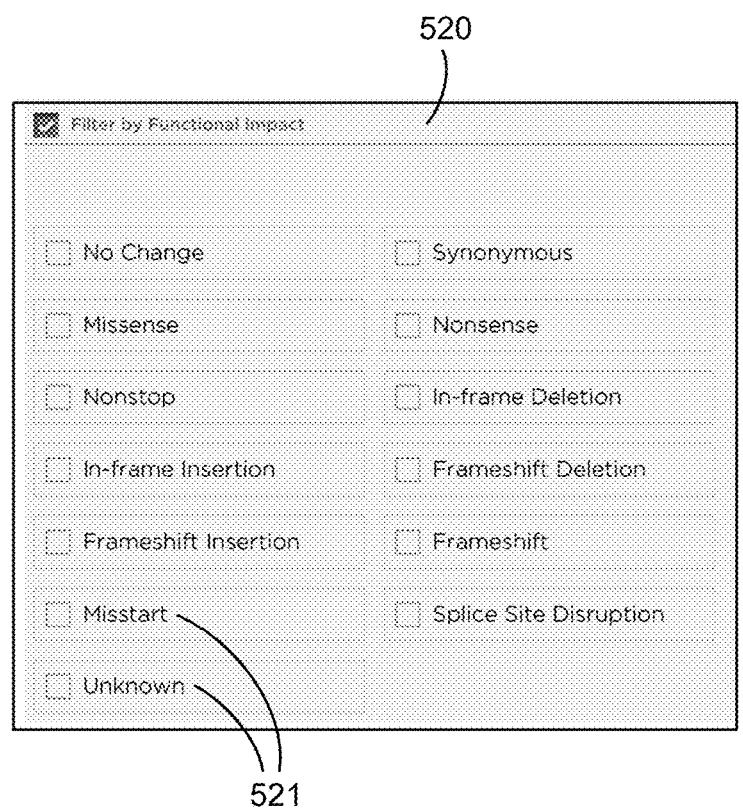
FIG. 5D shows a menu that allows the user to select variations depending on the effect on the encoded protein.

FIG. 5C is another type of filter provided by the system that allows the user to focus on particular chromosomal regions according to their function—either for genes positively selected as part of a panel, or across the entire genome. Thus, the user can select encoding regions (CDS), exons, untranslated regions (UTR) at the 5' end, the 3' end, or both, transcription regulators such as promoter or enhancer regions, and so on. FIG. 5D is a filter that allows the user to focus on particular types of genetic variations in terms of their predicted effects on the encoded protein. For example, small variations within an encoding sequence can be categorized as follows:

a gene alteration that results in selection of a codon synonym (hence no change on the encoded amino acid), in frame effects—e.g., alterations, deletions, or insertions that cause point variations but otherwise leave the encoded protein sequence intact, or more profound changes likely to compromise protein function, especially if they occur early in the coding sequence (for example, frame shift mutations or insertion of a stop codon).

By way of further illustration, small nucleotide variations (SNV) can be filtered according to predicted pathogenicity, gene region, impact on encoded amino acid sequence, SNV type (e.g., single nucleotide polymorphisms, deletions, insertions, multi-nucleotide substitutions), zygosity (homozygous or heterozygous), whether it is found in a particular database such as dbSNP, or to exclude commonly found variants in healthy populations. Copy number variations (CNV) can be filtered according to predicted pathogenicity, gene region, number of copies, repeat category overlap, or whether it is found in a particular database such as DGV. Any quality filters, such as ploidy quality score, and CNV type quality score. Different types of variations can be screened for quality or confidence of the sequencing and/or the sequence assembly so that sequencing errors do not confound the analysis. Such filters may be selected by the user for use in any effective combination, optionally in combination with a filter of the user's own devising that has been constructed on or loaded onto the system.

The computer system and methods of the invention can be implemented so as to provide annotations and further information to assist in drawing conclusions from the presence of genetic variations that are presented after filtering. For example, the server may provide algorithms to predict protein expression, protein function, clinical presentation, and/or disease risk in any combination. Protein expression can be predicted on the basis of the effect on the encoded amino acid sequence. Protein function can be predicted on the basis of predicted three-dimensional structure, and effects on catalytic and binding sites. Clinical presentation and disease risk can be predicted based on cumulative history of other known variations at or around the same location and their known effects. Such predictive algorithms can be programmed into the system, or sourced from external servers, for example, over the Internet.

The computer system and methods of the invention can also be implemented so as to provide comparisons with gene variations previously reported that either occur in the same genes or that have similar biological and/or clinical effects. The system can source such information from within its own records of similar analyses done on other complex sequences in the same customer and reference databases. The system can also source such information from other systems and databases that are external to the system, for example, over the Internet. Once such other known variations are identified, the system can indicate the position of each variation on the same genetic map and/or provide a nearby link to information known about each other known variant. The annotation function can be provided as both a passive and an active tool. Thus, upon receiving information on user preferences, the system may as a matter of course annotate the genetic map with information about nearby or related genetic variants using internal and/or externally obtained information, in accordance with the user preferences. Alternatively or in addition, the system may be set up with a query function. Thus, the user may select on one or more genetic variations in a test sequence, or one or more gene regions in the test or reference sequence. The system may then be prompted to run its own algorithms and/or seek external information in accordance with the request from the user.

The technology described here allows the user to take advantage of rich variant annotations. This can include (1) clinically meaningful variant names that follow HGVS standards; (2) gene annotations by transcript including functional impact and scores from prediction algorithms such as Polyphen and SIFT; (3) cross-reference annotations from several genomic databases such as dbSNP and DGV and (4) allele frequency information across several data sets such as the 1000 Genomes. The user can thereby be provided with consolidated information with smart links to additional resources. Information includes variant attributes, variant and gene annotations, technical performance summaries and context sensitive links including links to NCBI, PubMed and popular public genome browsers. Consolidated views help shorten the variant analysis and research process.

V. Social Networking

Another feature that can be implemented in the computer systems and methods of this disclosure is a platform for interacting with other users so as to improve the knowledge base, both with respect to a particular test sequence, and generally in the study of variations of a particular type or class.

This can be implemented using a server that provides information for multiple clients. In reference to FIG. 1A, each of the other clients 105 is provided with a display of a gene sequence map assembled by the server 104 for presentation to users, the gene sequence map showing variations in complex sequence for a test sample compared with complex sequence for one or more reference samples (such as in FIGS. 2A and 2B). An interface is provided whereby a first client user 103 can direct the server to make the gene sequence map, particular sequence data, or particular genetic variants available to other client users 105. Optionally, the first user annotates or selects particular genetic variations or gene regions of interest, and/or poses particular questions, for example, with respect to possible biological or clinical effect of one or more identified genetic variations, or generally seeking other experiences regarding the genetic variations or gene regions of a similar nature to those they have selected or researched. The information is annotated or linked to the display at or near the locus to which the variation has been mapped.

Having been granted access to the map or information from a particular test sample or particular genetic variants, other users on the system 105 (either members selected by the first user, subscribing members generally, or a member of the public who has access to the system over the Internet) can reflect on the nucleotide variations or the questions posed by the first user. Should they wish to contribute information in reply, the system provides a portal by which the reply information is transmitted to the first client user privately, or to the community of users selected by the first client user for general discussion of the topic. The portal can be implemented so as to permit the replying user to add a location marker and/or an annotation to the gene sequence map, or to append information to an annotation made by the first user. The portal can also be implemented so as to permit a discussion to occur through an exchange posting linked to the map or previous comments, or provided as a separate display whereby the first client user can receive reply information about one or more of the variations that the server obtains from one or more of the other client users.

Figure 8:
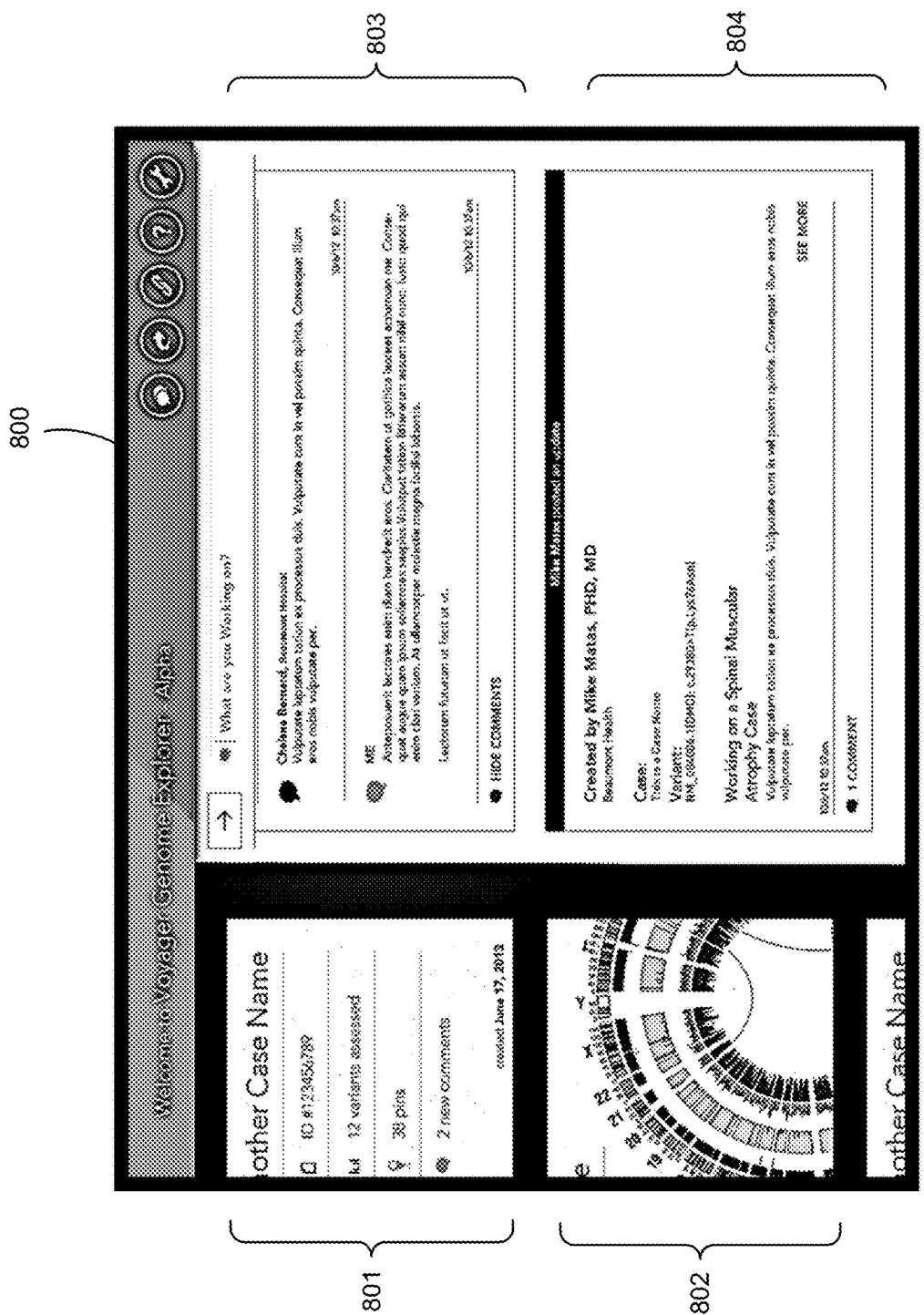
FIG. 8 shows a social networking portal that has been configured for promoting a dialog between a user that has analyzed a sequence for variations according to this invention, and other users who may have an interest in the variations observed or the genes in which they have occurred.

FIG. 8 is a screenshot of a sequence analysis system according to this invention that has been configured for promoting such a dialog. In this configuration, there is a window or portal 804 where the first user posts an informational overview about the sequence being displayed, such as the presence and import of variations detected therein. In another window or portal 803, other users authorized to have access post reply information, which can evoke further commentary from the first user and others. The first user may optionally be authorized by the system to control access and/or moderate and edit the discussion.

In more general terms, the system may provide forums of various types by which users may interact about particular genetic variations, particular gene regions, particular biological effects, or particular clinical issues. Such forums may be in the style of a bulletin board or blog, optionally with links to gene maps, complex sequence data, or other discussions in any combination, optionally with various levels of controlled access depending on privacy issues or proprietary aspects of gene sequence data and/or expert interpretation thereof. Such forums may also be in the style of a news feed with links to gene maps, complex sequence data, or other discussions in any combination, optionally with various levels of controlled access. News feeds will typically be provided by subscription, whereby certain users or class of users may be given access, and may opt in or opt out to receiving the selected feeds on a periodic or as-needed basis.

Such forums may also be in the style of a passive knowledge base or wiki, where the system provides a repository of information available for research into particular topics or genetic variants. The knowledge base may have links to gene maps, complex sequence data, or other discussions in any combination, optionally with various levels of controlled access, and optionally also provides a means by which the initiating user of each entry or other users may have authority to update, depending on their level of access.

Thus, the social networking aspect of the invention can be implemented so that as users filter and search for variants, they can mark variants of interest by highlighting or annotating them to get back to them easily. Community assessments allow users to contribute to and leverage community knowledge about the pathogenicity of variants. As users use the technology to create variant assessments, they can opt to share them with the community. Users can then comment on each other's assessments. The next time that variant is seen in the context of a case, users see a summary of all shared assessment as well as the detail of each assessment including who made the assessment, when and all the supporting notes, evidence and comments. Newsfeeds provide a way for users to stay on top of the latest activities and collaborate with other users. Colleagues can comment and collaborate with each other directly through the newsfeed to exchange information, solve cases and assess the pathogenicity of variants.

VI. Illustrative Example

The figures accompanying this description show a non-limiting illustration of certain aspects of the invention. The system for analyzing genetic variants shown in this illustration has been developed by Complete Genomics Inc. for use in commerce under the service mark Voyager™ or Voyager Genome Explorer™.

Voyager provides an application platform for use on a computer station, personal data assistant, touch pad, or other client configured for interaction with a server that provides sequence information and display. The platform may be implemented on standard operating systems such as iPad™, iOS™, Android™, and Windows™. The user opens up the application, logs in, and gets access to cases from the server to which the logged in user is permitted access. Voyager is integrated seamlessly with Complete Genomics' gene sequencing service. Thus, the credentialed user will have access to sequence data from samples they provided, sequence data that has been made generally available to Voyager subscribers and/or the general public.

A user having a complex sequence they want analyzed logs into the system once the sequence is available from the gene sequencing service. The sequence is labeled with information about the test sample: for example, nature of the sample (such as peripheral blood), the sampling date, and an identifier (ID) for the particular sample. The sequence is given its own Internal Accession Number that is unique to the sample and the sequencing run. Thus, samples from different patients, multiple samples from the same patient on different days, and different sequence runs for the same sequence are identified separately.

Upon launching or enquiring about complex sequence from a particular patient, the user is first presented with clinical context: differential diagnosis, phenotypes (collected at time of order using standard ontology from SNOmed); additional clinical information as available; pedigree information; identity of the treating and/or interpreting clinician. There are also areas to attach additional information (for example, laboratory results, and/or clinical or family history). The user may also look at technical summary to see quality of the sequence data: for example, information about the subject, a quality control report, and more detailed statistics about the data, such as genome vs. exome coverage, or summary of variants by various dimensions.

FIG. 2A is a screenshot 200 showing a display of genome sequence data from a particular patient on the right side 210 in a karyogram view. Each chromosome is numbered 211, and depicted according to its banding pattern 212. Beside each chromosome are markers that map variations determined by analysis of the test sequence. The display on the left side 220 provides a list of particular variations in a panel of genes of interest 221 which a user has selected for analysis, with a summary assessment underneath 222 as to whether it is pathogenic or benign. FIG. 2B is a screenshot 230 comprising a cytogenomic view 240 of the entire genome. Here, the data for each patient is compared with a sequence standard drawn from CGI's database. FIG. 3A is an overview display 300 of the entire genome sequence of the patient sample in the form of a circular or Circos®-style plot (M. Krzywinski et al., Genome Res. 19:1639-1645, 2009), with curved lines in the middle 301 depicting apparent interchromosomal junctions. FIG. 3B in this example provides a detail 310 for Chromosome 4.

FIG. 4A is a display showing a chromosome view 400 for Chromosome 1, selected for more detailed viewing by the user (for example, by selecting a particular chromosome from the karyogram display in FIG. 2A). The display in FIG. 4A shows the selected chromosome 401 at the top, with markers and thumb controls 402 showing the region depicted in the graphics below. The linear plots 403, 404, 405, and 406 provide a map within the selected region of the calculated copy number 403 (expected to be 2, except for inter-regional duplication), the calculated allele specific copy number 404 (expected to be 2 where homozygous and 1 where heterozygous), the occurrence of small nucleotide variations 405, and gene locations 406 (occurrence of open reading frames). From this view, the user can zoom in and out using top thumb controls 402. A double tap zooms in, whereas a finger double tap zooms out. By adjusting the position of the thumb controls 402, the user can zoom towards a subregion of interest within the previous range. Alternatively, the user may use the + and − buttons 407 on the right to zoom the image from the center of the chromosomal region.

FIG. 4B shows an alternative means by which a user may zoom in to a particular gene. The screenshot 410 shows a keyboard 412 called up by the user, which can then be used to type the name of a gene or location of interest into the search box 411. The system then selects the appropriate chromosome and zooms into the intrachromosomal region where the gene is located. The magnification is selected by the system to accommodate the known length of the gene (including introns, exons, and control sequences), centering the gene between flanking sequence on each side.

FIG. 4C is a display showing an expanded view 420 of a narrower region of Chromosome 17 421 between the markers 422 on the left. The user may reach this view by expanding a view of complete Chromosome 17, zooming in on a particular gene, or by searching for the gene by its name (TP53). Shown in this display are maps for two overlapping genes: TP53 426 which is oriented left to right 426, and a portion of WRAP53, which happens to partially overlap with TP53, and is oriented right to left 427. Each gene is depicted as a horizontal line with vertical lines on the 5' and 3' ends and a directional indicator ("<" or ">") indicating the orientation. Encoding regions for the unprocessed translation product are indicated in block form at the corresponding location within each gene.

FIG. 4D is a display 430 showing a further expanded view of a particular gene on Chromosome 14 431. The user may reach this level of expansion by expanding from a lower resolution as before, or by tapping on the particular SNV in a display at lower resolution (corresponding to the SNVs shown in strip 425 of FIG. 4C). Again, the copy number 433 and allele specific copy number 434 are shown. At this level of expansion, the genome sequence appears as single bases 435. The test sequence and reference sequence are the same, except where there is a variation: in this case, an SNV 437. The bottom-most graphic 436 is the encoded amino acid sequence depicted using the one-letter code.

FIGS. 5A, 5B, 5C, and 5D show menus for selecting filters that can be applied to the data, so as to simplify and focus the variations shown within the selected region. Sequence variations of particular interest are caused to be shown on the display, whereas other variations or less interest or sequencing noise are filtered out and do not appear.

FIG. 5A shows a menu of filters 500 to focus the analysis towards certain variants of potential interest or importance. The user may select specific genes 501 or specific chromosomal locations 502 for the analysis. Small nucleotide variations (SNV) can be filtered according to predicted pathogenicity, gene region, impact on encoded amino acid sequence, SNV type (e.g., single nucleotide polymorphisms, deletions, insertions, multi-nucleotide substitutions), zygosity (homozygous or heterozygous), whether it is found in a particular database such as dbSNP, to exclude commonly found variants in healthy populations, and sequencing quality filters (such as VQHIGH vs. VQLOW, and minimum read count). Heterozygous variants marked as VQHIGH generally require at least two high quality, well mapped reads per allele. Homozygous variants marked as VQHIGH generally require at least seven reads. Variants marked as VQLOW may have fewer reads supporting the call, and are accompanied by a lower score indicating the lower confidence in the call. Copy number variations (CNV) can be filtered according to predicted pathogenicity, gene region, number of copies, repeat category overlap, whether it is found in a particular external database such as DGV, and sequencing quality filters, such as ploidy quality score, and CNV type quality score.

FIG. 5B shows a menu 505 by which a user may assemble a gene panel of particular interest. In this case, a panel of 15 genes is selected. FIG. 5C shows a menu 510 where the user selects gene regions by function 511 that should be included in the analysis. Rather than showing the entire gene sequence, the user may select to appear the encoding region (CDS), upstream transcription start sites (TSS), introns, exon overlap at the 5' and/or 3' end, mRNA splicing donor and acceptor sites and untranslated regions (UTR) at the 5' and/or 3' end.

FIG. 5D shows a menu that allows the user to select SNVs depending on their effect 521 on the encoded protein or its expression: for example, no change, synonymous variations (silent mutations that result in no change in encoded amino acid sequence), nonsense variations (resulting in a premature stop codon), missense variations (resulting in a chance in a single amino acid), a misstart variation (resulting in misplacement of a start codon), in-frame insertions or deletions (resulting in a small change in amino acid sequence but leaving most of the protein intact), frameshift insertions or deletions (causing downstream nucleic acid sequence to be out of frame, thereby encoding an entirely different amino acid sequence), splice site disruption (preventing normal post-transcription processing), and unknown or unspecified variations.

In this implementation, the user has an option to apply the filters to either single nucleotide variations (SNVs), copy number variations (CNVs), or both. For SNVs, the user may restrict the analysis to variants where there is some information in the system which indicates its pathogenicity. Other SNV filters include gene region (what region the variant falls in, e.g. CDS, 5'UTR, 3'UTR), the functional impact (e.g. synonymous, missense, nonsense, or frameshift), SNV type (e.g., insertion, deletion, or substitution), zygosity (homozygous or heterozygous), dbSNP (whether it's found in dbSNP or not), minor Allele Freq for 1000 genomes to potentially filter out commonly found variants in healthy populations, and filters for sequence quality and minimum count. For CNVs, the user may select filters for CNV: whether they should be included (for example, CNVs greater than a given size), pathogenicity, copy number state, repeat category overlap (e.g. DNA, LINE, Low_Complexity, SINE, Satellite, SegDup, Self-chain, Simple_Repeats, scRNA, tRNA, snRNA), whether it appears in the Database of Genetic Variants (DGV), and quality filters (e.g., Ploidy Quality Score, CNV Type Quality Score). The Voyager system allows the user may create their own filter having filtering characteristics they desire.

Figure 6:
FIG. 6 shows a display with a summary of the analyzed data for selected genes characterized the effect of the nucleotide variations on the encoded protein.

FIG. 6 shows a display 600 with a summary of the analyzed data characterized by various dimensions of interest. Each of the genes 601 is tabulated against its predicted functional impact: whether the SNV is synonymous 602, causes no change 603, has an unknown or inconclusive result 604, constitutes a missense mutation 605, and the total 606. The numbers in the table are set up as links. If the user taps on a number, the variant list is filtered to show the selected variants. The user can tap on a gene next to Functional Impact Row to navigate back to previous screen, conducting a search and presenting an expanded display for the selected gene.

The system also provides links to external databases and browsers such as UCSC or Ensembl so that the user can investigate more details on gene structure or conservation information in a gene region of interest, look up information in GeneReviews or do a more global NCBI Search.

Figure 7:
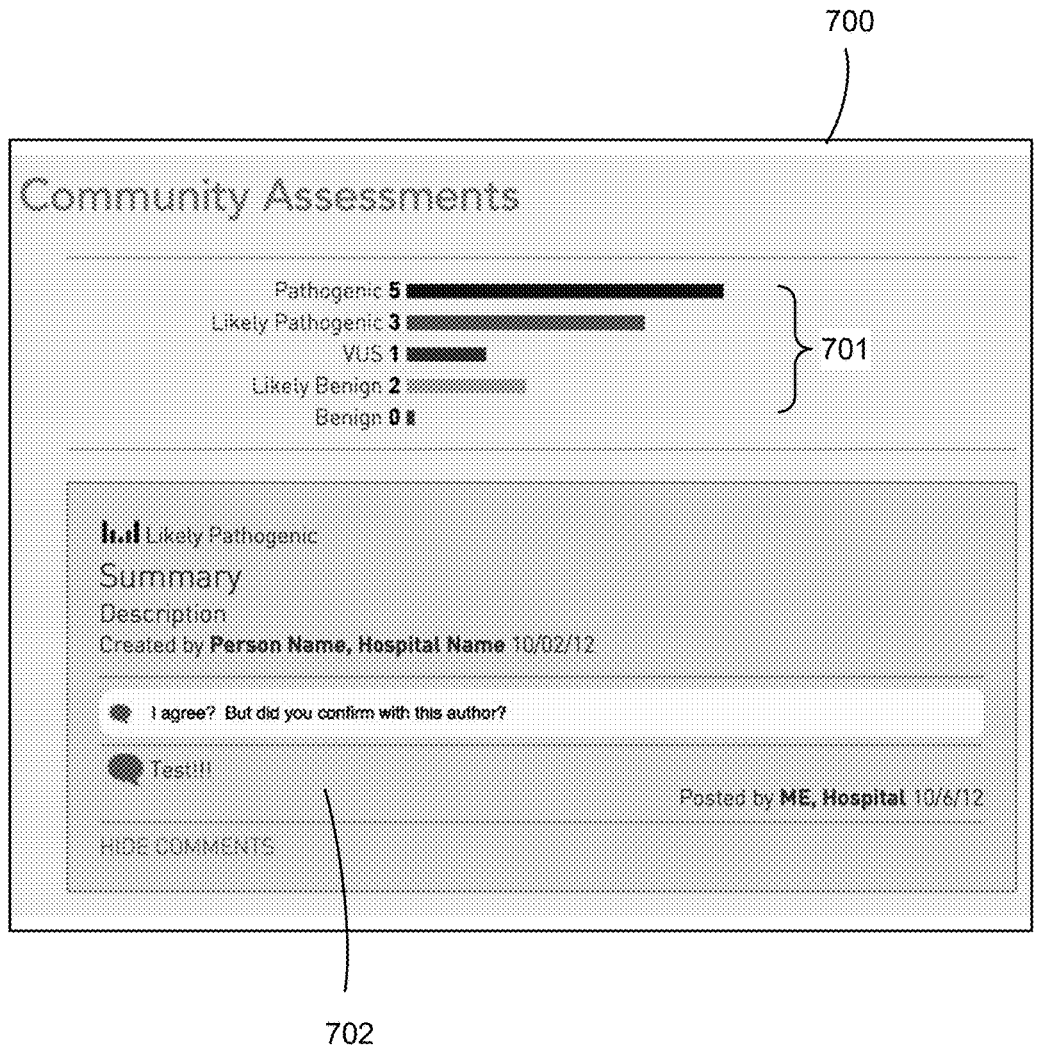
FIG. 7 shows a display in which a particular sequence variation has been evaluated by a community of users.

FIG. 7 shows a display 700 with a community assessment of a particular sequence variation that has been detected by comparing the test sequence to a reference sequence. At any time, the user can create an assessment to capture research notes and other evidence collected. When ready, the user may instruct the server to share the assessment with other users of the system. As users create and share assessments, Voyager then aggregates assessments for a particular variant across cases and provide an average community assessment for that variant. When that variant is seen again in a particular case, users can use this aggregate assessment as additional information in filtering, sorting and assessing variants to fit the context of the specific case.

The bar chart 701 shows the distribution of community assessments by rating. Underneath the chart, the user may access written comments 702 from each of the contributors to the assessment. As new assessments are created or comments are posted on assessments, other members of community get notifications that there is new activity. In the case when the user is not already logged into Voyager, they would see iPad notifications. If users is already in Voyager, they would see an indicator on a newsfeed icon presented as part of the display. Where the user is in the context of a specific case, the newsfeed is automatically filtered to community activity for the given case. There is also a newsfeed on the home page which shows activity across all cases.

FIG. 8 shows a screenshot 800 comprising a first window 801 summarizing the case with the number of variants, and indicating when there are new comments. A second window 802 shows a map of sequence variations shared with other users. A third window 804 provides information inputted from a first user, typically the user who supplied the sequence being discussed. A fourth window 803 is programmed and configured for exchange of commentary, where other users of the system post reply information, which can initiate further dialog from the first user and others.

VII. Flow of Information

Figure 9:
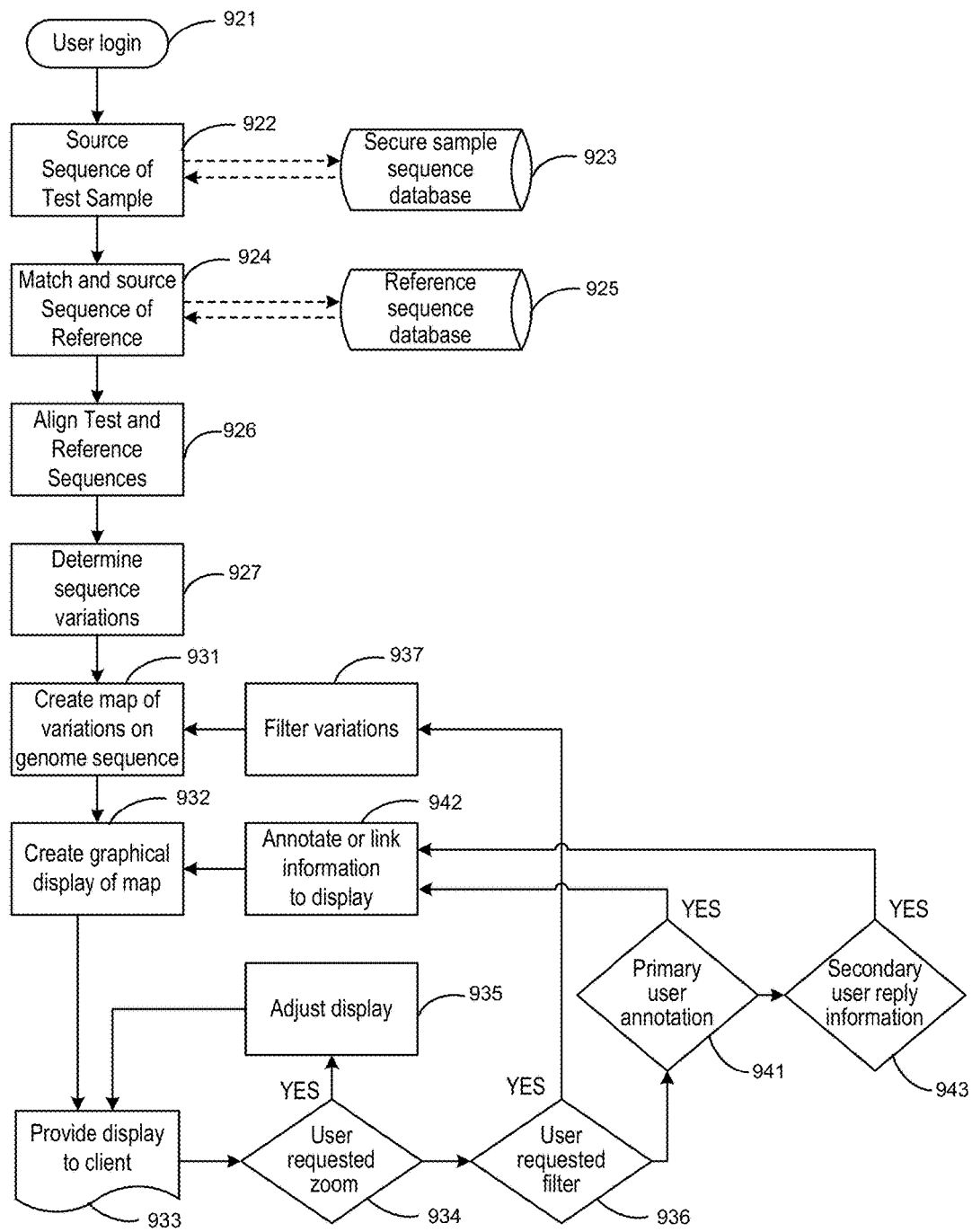
FIG. 9 is a flow chart showing an exemplary process of this invention by which a user may submit a sequence for processing and obtain a display with the resulting analysis.

FIG. 9 is a flow chart showing a system and process by which a user may submit a sequence for processing and obtain a display with the resulting analysis. After the user has securely logged in to the system 921, they present a sequence from a test sample 922 stored in a secure sample sequence database 923. The user may then select one or more particular reference sequences 924 from a reference database 925 that matches the test sequence, or let the server select reference sequence(s) that are appropriate. The test and reference sequences are then aligned 926, and sequence variations are identified 927.

The server then creates a map of variations 931, in which differences between the test and reference sample(s) are located in relation to known chromosomal markers. The server then compiles a graphical display 932 of the variations, which is then presented to the client 933. The display may be presented in a certain preselected chromosomal region of interest. Alternatively, as described in more detail below, the differences can be presented according to the scope of the test sequence (for example, a karyogram or chromosome view), from which the user may zoom in to focus on the details of a particular region 934, or zoom back out. The display is adjusted 935, and presented to the client 933 according to the request. As described below, the user may also request one or more filters 936 which are used to select variations between the test and reference samples 937 which are significant or of particular interest. The variations remaining after the filters are then used to create a map 931 and a graphical display 932 for display to the client 933. The user may provide their own annotation 941 for each variation which is incorporated 942 into the display 932. In a multi-user system, other users may reply 943 to the first user's annotation. The reply information is then incorporated into the display 942 either as a direct annotation or as a linked comment.

VIII. Computer Implementation

As a general matter, computer systems referred to in the context of this invention, their design, manufacture, control, and programming may be conducted according to any suitable technology. Any of the computer systems referred to in this disclosure can use any suitable number of subsystems. A computer system may include a single computer apparatus, where the subsystems can be the components of the computer apparatus. Alternatively, a computer system can include multiple computer apparatuses, each being a subsystem, with internal components.

Figure 10:
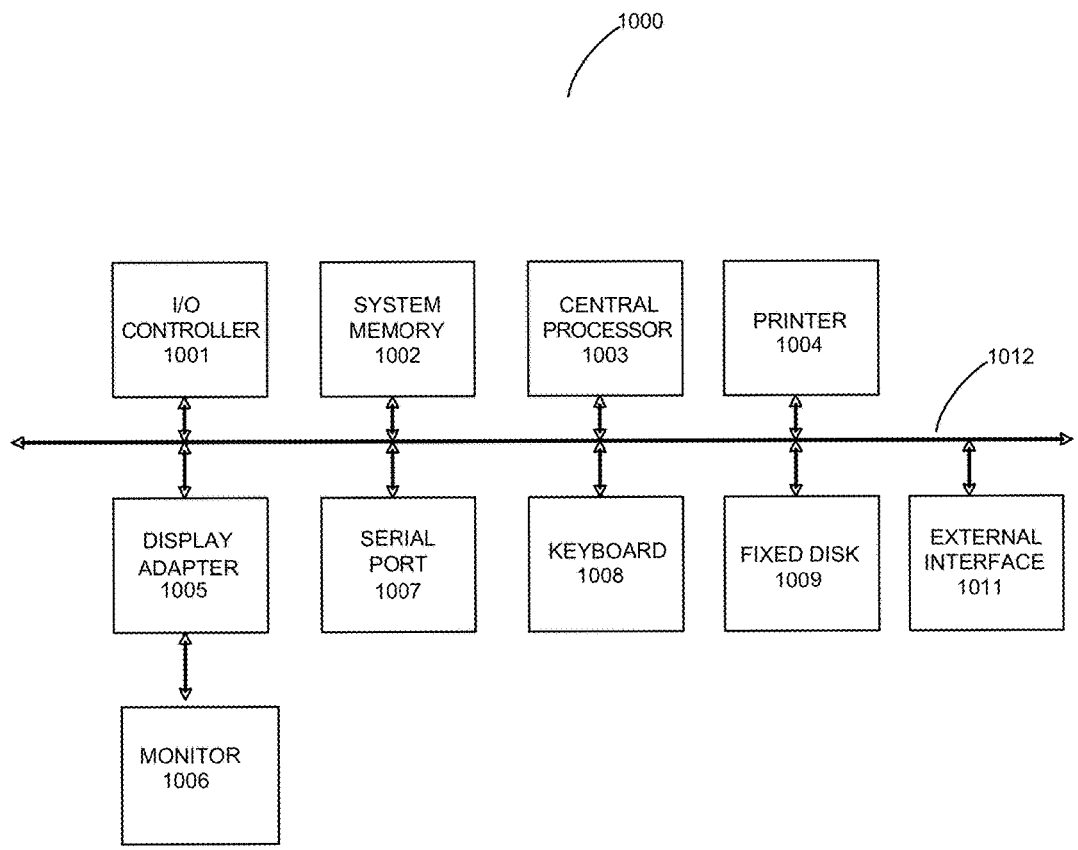
FIG. 10 shows the subsystem architecture of a computer by which a gene explorer system according to this invention may be implemented.

The subsystems shown in FIG. 10 are interconnected via a system bus 1012. Additional subsystems such as a printer 1004, keyboard 1008, fixed disk 1009, monitor 1006, which is coupled to display adapter 1005, and others are shown. Peripherals and input/output (I/O) devices, which couple to I/O controller 1001, can be connected to the computer system by any number of means known in the art, such as serial port 1007 (e.g. USB). For example, serial port 1007 or external interface 1011 can be used to connect computer system 1000 to a wide area network such as the Internet, a mouse input device, or a scanner. The interconnection via system bus 1012 allows the central processor 1003 to communicate with each subsystem and to control the execution of instructions from system memory 1002 or the fixed disk 1009, as well as the exchange of information between subsystems. The system memory 1002 and/or the fixed disk 1009 may embody a computer readable medium. Any of the values mentioned herein can be output from one component to another component and can be output to the user.

A computer system can include a plurality of the same components or subsystems connected together by external interface 1011 or by an internal interface. Optionally, computer systems, subsystem, or apparatuses can communicate over a network. In such instances, one computer can be considered a client and another computer a server, where each can be part of a same computer system. A client and a server can each include multiple systems, subsystems, or components.

Any of the embodiments of the invention can be implemented in the form of control logic using hardware and/or using computer software in a modular or integrated manner. Any of the software components or functions in this disclosure may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), or flash memory. The computer readable medium may be any combination of such storage or transmission devices.

Computer programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (for example, via Internet download). Any such computer readable medium may reside on or within a single computer program product (such as a hard drive, a CD, or an entire computer system), and may be present on or within different computer program products within a system or network. A computer system may include a monitor, printer, or other suitable display for providing interaction and display with the user.

Any of the methods referred to in this disclosure may be totally or partially performed with a computer system including a processor, which can be configured to perform the steps. Thus, embodiments can be directed to computer systems configured to perform the steps of any of the methods described here, potentially with different components performing a respective steps or a respective group of steps. Although presented as numbered steps, steps of methods herein can be performed at a same time or in a different order. Portions of these steps may be used with portions of other steps from other methods. Also, all or portions of a step may be optional. Additionally, any of the steps of any of the methods can be performed with modules, circuits, or other means for performing these steps.

The invention has been described and illustrated in this disclosure with reference to particular embodiments for the benefit and convenience of the reader. Discussion of various aspects of products and methods does not limit manufacture or use of the claimed invention except where expressly indicated.

The devices and methods of the invention may be substituted and adapted for use in different contexts for different objectives using different materials, elements, and steps without undue experimentation, thus achieving any or all of the benefits of the invention without departing from the scope of what is claimed.

In the United States of America and elsewhere as permitted by law, each publication and patent document cited in this disclosure is incorporated into the disclosure by reference in its entirety for all purposes.

What is claimed is:

1. A method for displaying variations between sequences by a computer system, the method comprising performing, by the computer system:
    (a) receiving a sample complex sequence for a test sample;
    (b) aligning the sample complex sequence with a reference complex sequence for a reference sample, the sample complex sequence and the reference complex sequence spanning at least one chromosome;
    (c) identifying a plurality of variations between the sample complex sequence and the reference complex sequence;
    (d) displaying a comparative gene sequence map at a user interface including a display screen of the computer system, the display screen showing where the plurality of variations are located within the sample complex sequence;
    (e) displaying a menu of filters on the display screen of the user interface, the menu of filters for use in adapting the display of the comparative gene sequence map with respect to the plurality of variations;
    (f) receiving, at the user interface via an input device of the computer system, a selection of a filter from the menu of filters, wherein the filter specifies one or more characteristics of variations to be displayed, the one or more characteristics including at least one of: one or more regions of the reference complex sequence and one or more effects on expression;
    (g) adapting the comparative gene sequence map displayed by the user interface to highlight variations having the one or more characteristics and/or remove variations not having the one or more characteristics specified by the filter, thereby providing filtered variations;
    (h) receiving at the user interface an assessment of one or more of the filtered variations; and
    (i) adapting the filter for subsequent use by the computer system to include or exclude one or more of the filtered variations according to the assessment.

2. The method of claim 1, wherein the plurality of variations includes copy number variations (CNVs), small nucleotide variations (SNVs), and loss of heterozygosity (LOH).

3. The method of claim 1, further comprising:
    receiving, at the user interface, a selection of a region within the comparative gene sequence map, the region being less than half the comparative gene sequence map; and
    reconfiguring the display of the comparative gene sequence map such that the region is magnified and variations of the sample complex sequence in the region are provided in the display, wherein the display presents separate graphs across the region for copy number, allele specific copy number, and protein encoding sequences.

4. The method of claim 1, wherein the user interface is configured to provide selectable options of a karyogram view, a circular view across one or more chromosomes, or a linear view of a region of interest, any of which indicate where variations in the sample complex sequence occur, and
    wherein, for the karyogram view, copy number gain and copy number loss are depicted with opposite arrows next to regions having such copy number variations.

5. The method of claim 1, wherein step (a) comprises:
    (i) receiving a first identifier identifying a user and a second identifier identifying a test sample;
    (ii) determining whether the user has authority to access sequence data for the test sample; and if so, (iii) retrieving complex sequence for the test sample from a secure database, the secure database including genomes for a plurality of different samples.

6. The method of claim 1, wherein step (a) comprises sequencing DNA contained in the test sample, thereby obtaining sample complex sequence for the test sample.

7. The method of claim 1, wherein step (b) comprises iteratively:
    (i) sourcing a potential reference sequence for any one of a plurality of a reference samples in a reference database;
    (ii) comparing the potential reference sequence for the test sample with the sample complex sequence sourced in step (i); and
    (iii) selecting the potential reference sequence sourced in step (i) as a suitable reference sequence for analyzing the sample complex sequence for the test sample if it matches the test sample according to preset criteria.

8. The method of claim 1, further comprising predicting one or more effect(s) of each of at least some of the variations identified in step (c) on protein expression, protein function, clinical presentation, and/or disease risk, and providing information about the effect(s) with the comparative gene sequence map in step (d).

9. The method of claim 1, further comprising comparing at least some of the variations identified in step (c) with known variants, and providing information about the known variants with the comparative gene sequence map in step (d).

10. The method of claim 9, wherein the information about the known variants has been obtained at least in part from external databases.

11. The method of claim 1, wherein the menu of filters includes filters for all of the following:
    gene region;
    type of small nucleotide variation (SNV);
    CNVs greater than a given size;
    zygosity;
    impact on an amino acid sequence encoded at and around a variation;
    number of copies of the variation;
    amount of copy overlap;
    occurrence of the variation in an external database of variations;
    clinical presentation associated with the variation; and
    quality or confidence of the sample complex sequence at and around the variation.

12. The method of claim 1, comprising automatically identifying sequencing errors in the sample complex sequence, and removing such errors from the display.

13. The method of claim 1, wherein the computer system is connected with and is configured to access all of the following:
- an external database that provides a library of complex sequences for comparison with the sample complex sequence;
- an external database that provides a library of previously known sequence variations for comparison with variations in the sample complex sequence; and
- an external database that provides assessments of previously known sequence variations.

14. The method of claim 1, wherein the computer system is configured to provide a plurality of external user interfaces and to exchange and display assessments between the plurality of external user interfaces.

15. The method of claim 1, wherein the sample complex sequence and the reference complex sequence span a human genome.

16. A method for displaying variations between complex sequences by a computer system, the method comprising performing, by the computer system:
   (a) receiving a sample complex sequence for a test sample;
   (b) aligning the sample complex sequence with a reference complex sequence for a reference sample, the sample complex sequence and the reference complex sequence spanning at least one chromosome;
   (c) identifying a plurality of variations between the sample complex sequence and the reference complex sequence;
   (d) displaying a comparative gene sequence map at a user interface of the computer system, the display showing where the plurality of variations are located within the complex sequence;
   (e) receiving, at the user interface, a selection of a plurality of filters from a library of such filters provided by the computer system to obtain selected filters;
   (f) for each of the selected filters, adapting the comparative gene sequence map displayed by the user interface by removing variations not having characteristics specified by the respective filter, leaving filtered variations;
   (g) receiving, at the user interface, a selection of variations of interest from amongst the filtered variations on the comparative gene sequence map;
   (h) transmitting, via a network interface of the computer system in communication with a server, the variations of interest to other user interfaces of other computer systems;
   (i) receiving, via the network interface, comments pertaining to one or more of the variations of interest from one or more of the other user interfaces; and
   (j) displaying the comments from the other user interfaces on the user interface.

17. The method of claim 16, further comprising providing on the comparative gene sequence map displayed in step (d) at or near each of one or more of the variations identified in step (c) a hyperlink to a forum whereby a plurality of users having access to the sample complex sequence may exchange first information and reply information regarding the respective variation.

18. A method for displaying variations between complex sequences by a computer system, the method comprising:
   (a) receiving a sample complex sequence for a test sample;
   (b) aligning, with the computer system, the sample complex sequence with a reference complex sequence for a reference sample, the sample complex sequence and the reference complex sequence spanning at least one chromosome;
   (c) identifying, with the computer system, a plurality of variations between the sample complex sequence and the reference complex sequence;
   (d) identifying, with the computer system, variations within the plurality that are sequence read errors or sequence assembly errors;
   (e) removing from the plurality of variations identified in step (c) the sequence read errors and sequence assembly errors identified in step (d), thereby producing a refined plurality of variations;
   (f) displaying a comparative gene sequence map at a user interface, the display showing where the refined plurality of variations are located within the complex sequence;
   (g) receiving, at the user interface, a selection of a plurality of filters from a library of such filters provided by the computer system to obtain selected filters;
   (h) for each of the selected filters, adapting the comparative gene sequence map displayed by the user interface by removing variations not having characteristics specified by the respective filter, leaving filtered variations;
   (i) receiving, at the user interface, a selection of a region within the comparative gene sequence map, the region being less than half the comparative gene sequence map and including at least one of the filtered variations; and
   (j) reconfiguring the display of the comparative gene sequence map such that the region is magnified, wherein the region is magnified in proportion to a size of the region, and wherein the user interface includes two graphical markers that respectively define a starting location and an ending location of the region and that move to allow a user to change the starting location and the ending location.

19. The method of claim 18, wherein the refined plurality of variations has been screened to remove variations based on quality or confidence of sequencing or sequence assembly.

20. The method of claim 18, wherein the selection of the region within the comparative gene sequence map to magnify includes:
   displaying a variation on a touchpad display of the computer system; and
   receiving a tap on the touchpad display on the variation.

21. The method of claim 18, further comprising:
   determining whether the region is smaller than a specified size; and
   if the region is smaller than the specified size:
      displaying a nucleotide sequence that spans the region,
      displaying locations of one or more variations in the nucleotide sequence and
      displaying a variant nucleotide at a location corresponding to a single nucleotide variation in the nucleotide sequence.

* * * * *